(12) United States Patent
Nakamura et al.

(10) Patent No.: US 8,721,964 B2
(45) Date of Patent: May 13, 2014

(54) ANIMAL BLOOD CELL MEASURING APPARATUS

(75) Inventors: Yoichi Nakamura, Kobe (JP); Hideki Hirayama, Akashi (JP); Hideaki Matsumoto, Takasago (JP); Keiko Moriyama, Kobe (JP)

(73) Assignee: Sysmex Corporation, Kobe (JP)

( * ) Notice: Subject to any disclaimer, the term of this patent is extended or adjusted under 35 U.S.C. 154(b) by 435 days.

(21) Appl. No.: 12/727,938

(22) Filed: Mar. 19, 2010

(65) Prior Publication Data

US 2010/0248349 A1  Sep. 30, 2010

(30) Foreign Application Priority Data

Mar. 24, 2009  (JP) .................................. 2009-072646

(51) Int. Cl.
*G01N 33/00*  (2006.01)
(52) U.S. Cl.
USPC ........................... 422/63; 422/68.1; 422/82.03
(58) Field of Classification Search
USPC ....................................... 422/63, 68.1, 82.03
See application file for complete search history.

(56) References Cited

U.S. PATENT DOCUMENTS

| | | |
|---|---|---|
| 5,117,357 A | 5/1992 | Inoue |
| 7,580,120 B2 | 8/2009 | Hamada et al. |
| 2005/0219527 A1 * | 10/2005 | Ikeuchi et al. ................ 356/339 |
| 2006/0004530 A1 | 1/2006 | Miyamoto et al. |
| 2008/0241911 A1 | 10/2008 | Ueno et al. |

FOREIGN PATENT DOCUMENTS

| | | |
|---|---|---|
| JP | 01-312443 A | 12/1989 |
| JP | 2008-241672 A | 10/2008 |

OTHER PUBLICATIONS

Reagan et al. "Flow Cytometric Analysis of Feline Reticulocytes", Vet Pathol, vol. 29, pp. 503-508, 1992.*
Perkins et al. "Flow Cytometric Analysis of Punctate and Aggregate Reticulocyte Responses in Phlebotomized Cats", American Journal of Veterinary Research, vol. 56, No. 12, pp. 1564-1569, 1995.*
Cowgill, Elizabeth S. et al., "Clinical application of reticulocyte counts in dogs and cats," Vet. Clin. Small Anim., vol. 33, 2003, pp. 1223-1244.

* cited by examiner

*Primary Examiner* — Sam P Siefke
(74) *Attorney, Agent, or Firm* — Brinks Gilson & Lione

(57) ABSTRACT

An animal blood cell measuring apparatus comprising: a specimen preparation section for preparing a measurement specimen from blood of an animal; a characteristic information obtaining section for obtaining characteristic information indicating a characteristic of the measurement specimen, from the measurement specimen prepared by the specimen preparation section; and a controller configured for performing operations comprising: (a) classifying aggregate reticulocytes contained in the blood from other blood cells, based on the characteristic information obtained by the characteristic information obtaining section; and (b) outputting information regarding a number of the classified aggregate reticulocytes.

10 Claims, 18 Drawing Sheets

ANIMAL BLOOD CELL MEASURING APPARATUS

RELATED APPLICATIONS

This application claims priority under 35 U.S.C. §119 to Japanese Patent Application No. JP2009-072646 filed on Mar. 24, 2009, the entire content of which is hereby incorporated by reference.

BACKGROUND OF THE INVENTION

1. Field of the Invention

The present invention relates to an animal blood cell measuring apparatus.

2. Description of the Related Art

In making diagnoses on animals, counting reticulocytes is useful for diagnosing animals with, for example, anemia. At veterinary hospitals, currently, counting of red blood cells or white blood cells is often automatically performed using analyzers; however, reticulocytes are visually counted in general.

United States Patent Publication No. 2006/0004530 discloses an analyzer for automatically counting animal reticulocytes. The analyzer of United States Patent Publication No. 2006/0004530 receives the selection of an animal species to be analyzed, and counts blood cells based on analysis conditions corresponding to the received selection of the animal species. Here, blood cells to be counted include reticulocytes in addition to red blood cells, white blood cells, and the like.

Reticulocytes of some animal species consist of a single type of reticulocytes. However, for example, reticulocytes in felines consist of a plurality of types of reticulocytes including punctate and aggregate reticulocytes. Counting aggregate reticulocytes is useful when diagnosing animal species with anemia, whose reticulocytes consist of a plurality of types of reticulocytes. For example, in the case of felines, the number of punctate reticulocytes reaches a peak within 10 to 20 days after an episode of acute blood loss. Thereafter, the punctate reticulocytes disappear over approximately four weeks. Whereas, the number of aggregate reticulocytes reaches a peak within 4 to 7 days after the episode of acute blood loss. Accordingly, counting aggregate reticulocytes, the number of which reaches a peak at an earlier stage than the punctate reticulocytes, is useful, for example, for determining the degree of recovery from anemia (i.e., useful for determining the effect of medication).

As mentioned above, there are known analyzers that automatically count reticulocytes. However, United States Patent Publication No. 2006/0004530 does not give a description in relation to counting only aggregate reticulocytes among reticulocytes consisting of a plurality of types of reticulocytes. Therefore, even if the analyzer disclosed in United States Patent Publication No. 2006/0004530 is used, aggregate reticulocytes have to be visually counted, which imposes a substantial burden on veterinarians and laboratory technicians.

SUMMARY OF THE INVENTION

A first aspect of the present invention is an animal blood cell measuring apparatus comprising: a specimen preparation section for preparing a measurement specimen from blood of an animal; a characteristic information obtaining section for obtaining characteristic information indicating a characteristic of the measurement specimen, from the measurement specimen prepared by the specimen preparation section; and a controller configured for performing operations, comprising: (a) classifying aggregate reticulocytes contained in the blood from other blood cells, based on the characteristic information obtained by the characteristic information obtaining section; and (b) outputting information regarding a number of the classified aggregate reticulocytes.

A second aspect of the present invention is an animal blood cell measuring apparatus comprising: a specimen preparation section for preparing a measurement specimen from blood of an animal; a characteristic information obtaining section for obtaining characteristic information indicating a characteristic of the measurement specimen, from the measurement specimen prepared by the specimen preparation section; an aggregate-type classifying section for classifying aggregate reticulocytes contained in the blood from other blood cells, based on the characteristic information obtained by the characteristic information obtaining section; and an output section for outputting information regarding a number of the aggregate reticulocytes classified by the aggregate-type classifying section.

A third aspect of the present invention is animal blood cell measuring apparatus, comprising: a specimen preparation section for preparing a measurement specimen from blood of an animal; a characteristic information obtaining section for obtaining characteristic information indicating a characteristic of the measurement specimen from the measurement specimen prepared by the specimen preparation section; a selector for selecting an animal species to be measured, from at least a first animal species and a second animal species; and a controller configured for performing operations, comprising: (a) receiving a selection of the animal species selected by the selector; (b) classifying reticulocytes contained in the blood from other blood cells based on the characteristic information obtained by the characteristic information obtaining section, in response to the received selection of the animal species; and (c) outputting information regarding a number of the classified reticulocytes.

DETAILED DESCRIPTION OF THE PREFERRED EMBODIMENTS

Hereinafter, an animal blood cell measuring apparatus according to an embodiment of the present invention will be described with reference to the accompanying drawings. In the description below, from among features of the animal blood cell measuring apparatus, features relating to counting of reticulocytes are mainly described, and descriptions of features relating to measurement of white blood cells and the like are omitted.

Figure 1:
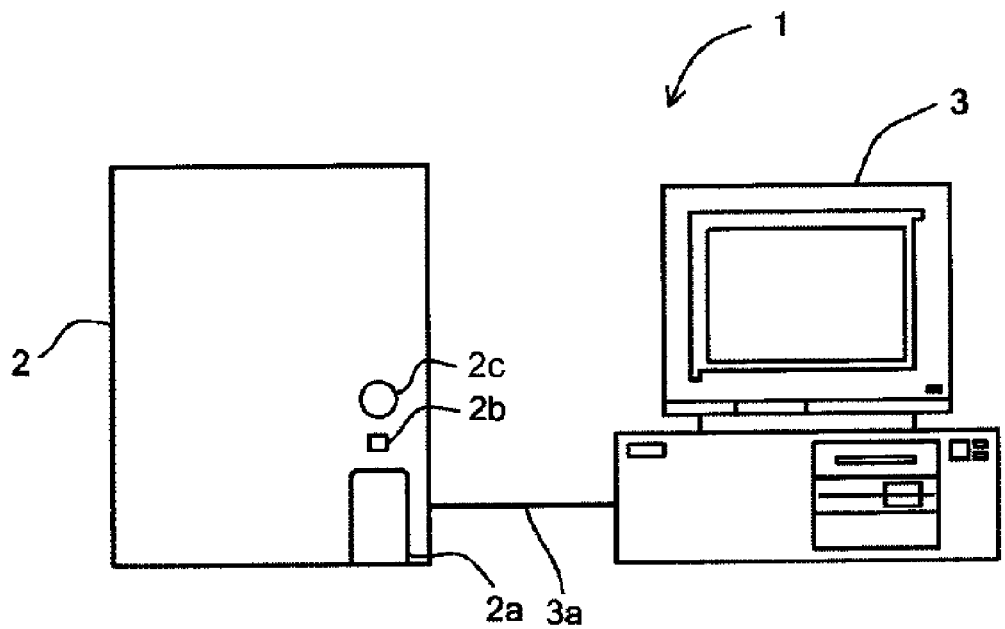
FIG. 1 is a front view showing a schematic structure of a blood cell measuring apparatus according to an embodiment of the present invention.

FIG. 1 is a front view showing a schematic configuration of the animal blood cell measuring apparatus according to the present embodiment. As shown in FIG. 1, main components of a blood cell measuring apparatus 1 according to the present embodiment are a measurement unit 2 and a data processing unit 3. The measurement unit 2 performs predetermined measurement on blood components contained in a blood sample, and transmits measurement data to the data processing unit 3. The data processing unit 3 performs an analysis process based on the measurement data, and displays analysis results on a monitor. The blood cell measuring apparatus 1 is installed in a veterinary hospital, for example.

The measurement unit 2 and the data processing unit 3 are connected via a data transmission cable 3a so that the measurement unit 2 and the data processing unit 3 can perform data communication therebetween. Note that the connection formed between the measurement unit 2 and the data processing unit 3 is not limited to a direct connection formed by the data transmission cable 3a. For example, the measurement unit 2 and the data processing unit 3 may be connected via a dedicated line using a telephone line, via a LAN, or via a communication network such as the Internet.

Figure 2:
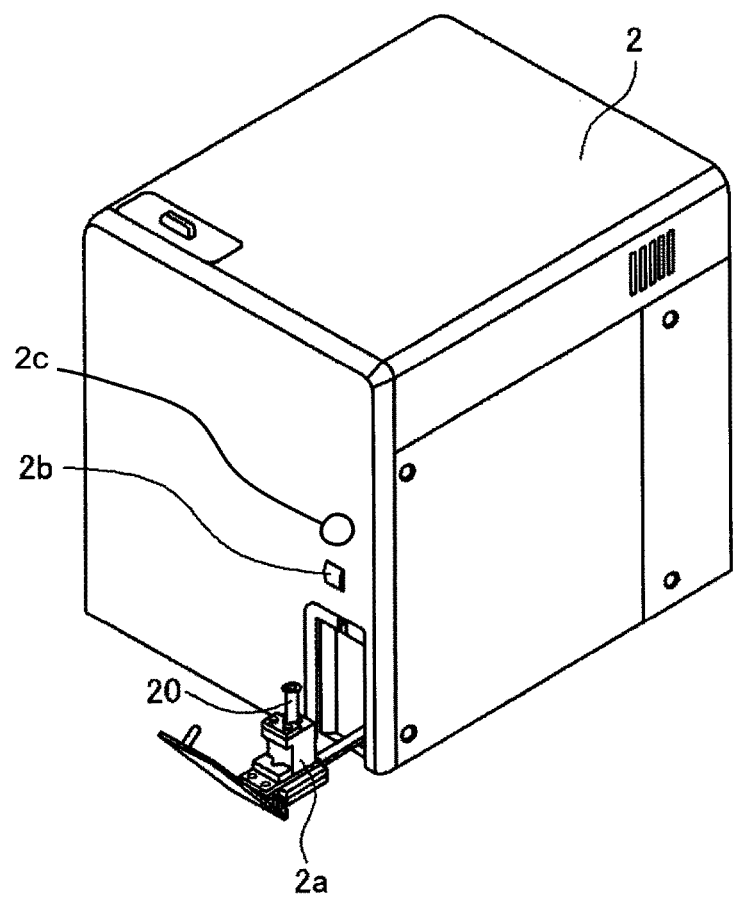
FIG. 2 is a perspective external view of a measurement unit according to the embodiment.

FIG. 2 is a perspective external view of the measurement unit 2. As shown in FIG. 2, provided at the lower right of the front face of the measurement unit 2 is a blood collection tube setting part 2a on which a blood collection tube 20 containing a blood specimen can be set. When a user presses a push button switch 2b provided near the blood collection tube setting part 2a, the blood collection tube setting part 2a opens and protrudes forward. This allows the user to set the blood collection tube 20 on the blood collection tube setting part 2a. When the user presses the button switch 2b again after the blood collection tube 20 is set, the blood collection tube setting part 2a recedes and closes. On the front face of the measurement unit 2, a start button 2c for starting sample measurement is also provided.

Figure 3:
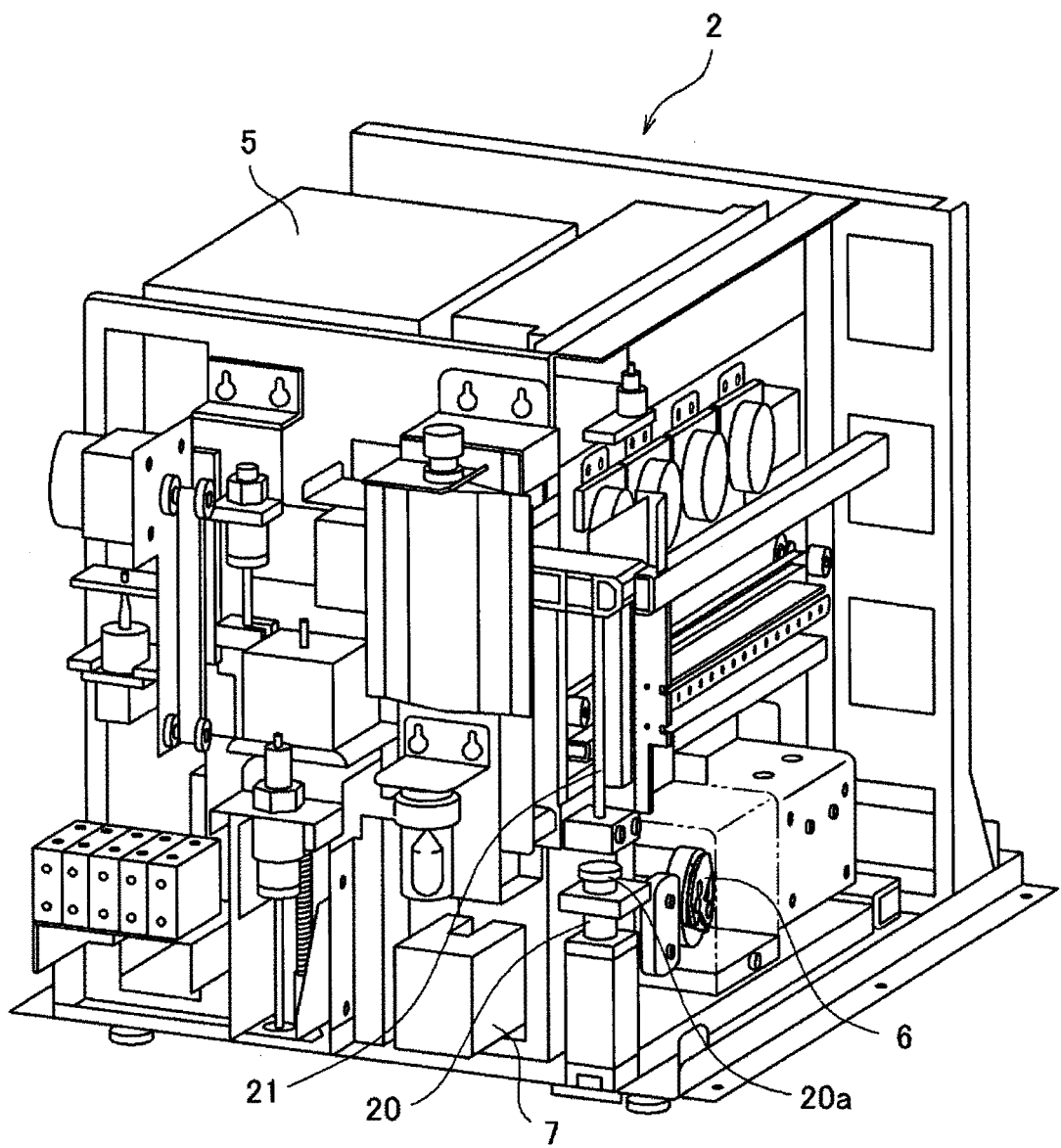
FIG. 3 is a perspective view showing an internal structure of the measurement unit according to the embodiment.
Figure 4:
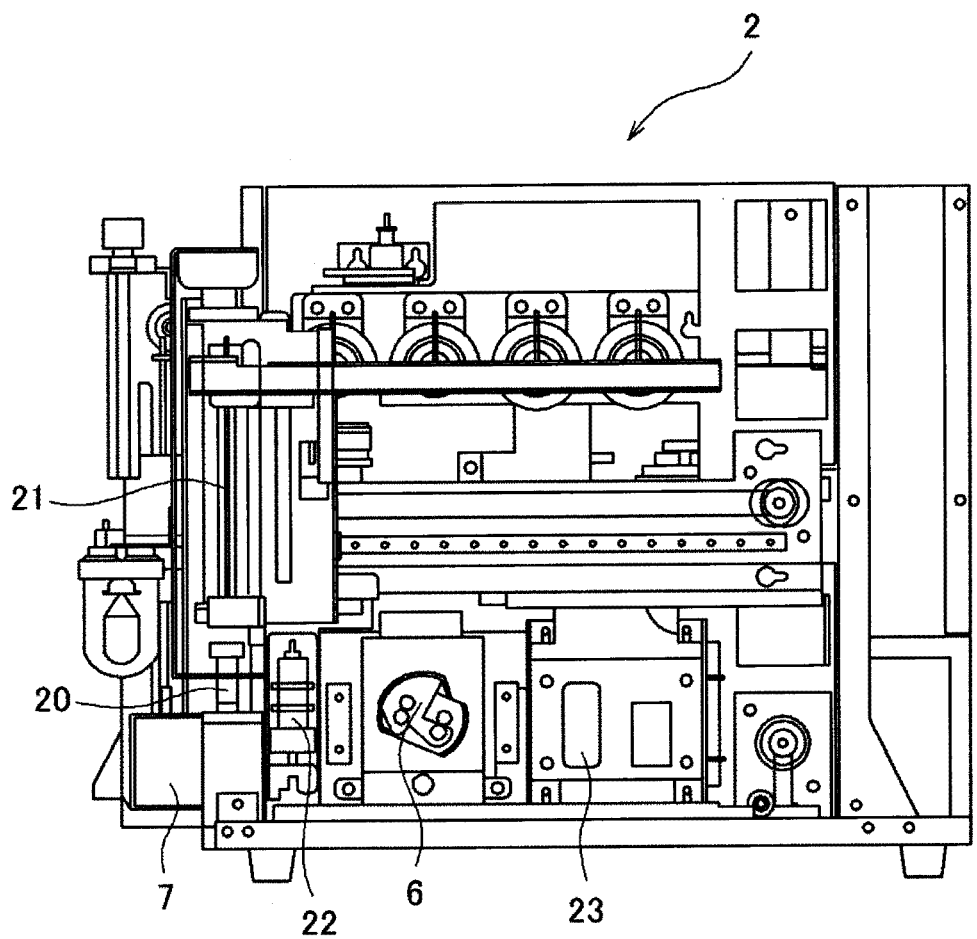
FIG. 4 is a side view showing the internal structure of the measurement unit according to the embodiment.

FIG. 3 is a perspective view showing an internal structure of the measurement unit 2. FIG. 4 is a side view of the internal structure.

The blood collection tube setting part 2a, on which the blood collection tube 20 is set, is accommodated within the measurement unit 2 in the above-described manner. Accordingly, the blood collection tube 20 is positioned at a predetermined aspirating position. Provided within the measurement unit 2 are: a pipette 21 for aspirating the blood specimen; and a specimen preparation section 4 that has, for example, chambers 22 and 23 for mixing the blood and reagents.

The pipette 21 has a tubular shape extending in the vertical direction, and has a sharp-pointed tip. The pipette 21 is connected to a syringe pump that is not shown. The pipette 21 is capable of aspirating and discharging a predetermined amount of liquid through operation of the syringe pump. The pipette 21 is further connected to a moving mechanism, and accordingly, is movable in the vertical and front-rear directions.

The blood collection tube 20 is sealed with a rubber cap 20a. The sharp tip of the pipette 21 pierces through the cap, which allows the pipette 21 to aspirate, by a predetermined amount, the blood specimen contained in the blood collection tube 20. As shown in FIG. 4, the chambers 22 and 23 are provided behind the blood collection tube setting part 2a. The pipette 21 having aspirated the blood specimen is moved by the moving mechanism and then discharges the blood specimen into the chambers 22 and 23. In this manner, the blood specimen is supplied to the chambers 22 and 23.

Figure 5:
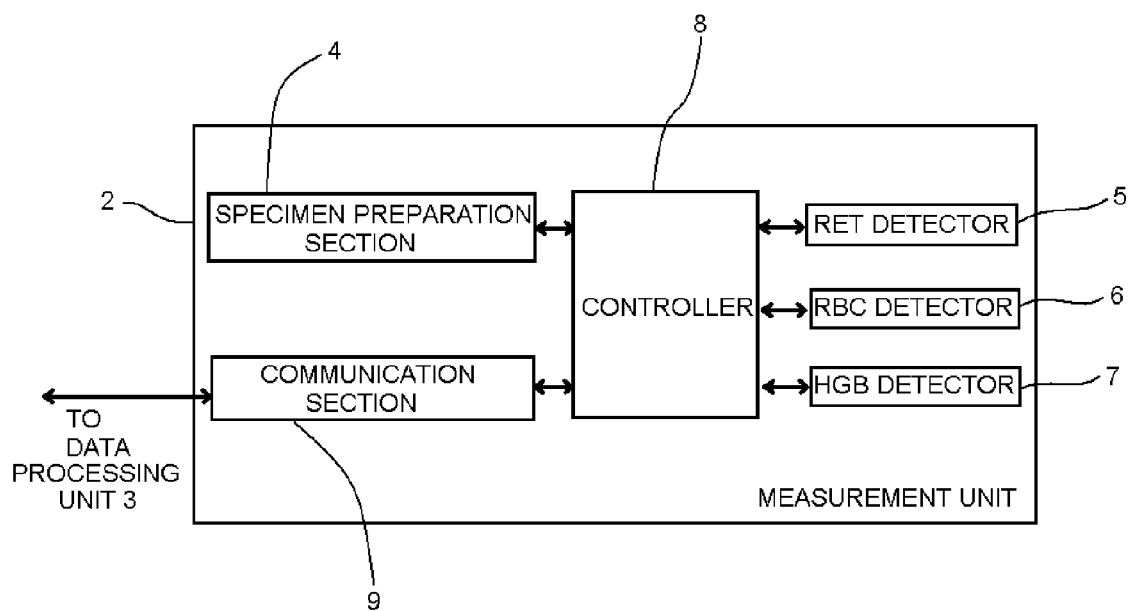
FIG. 5 is a block diagram showing a configuration of the measurement unit according to the embodiment.
Figure 6:
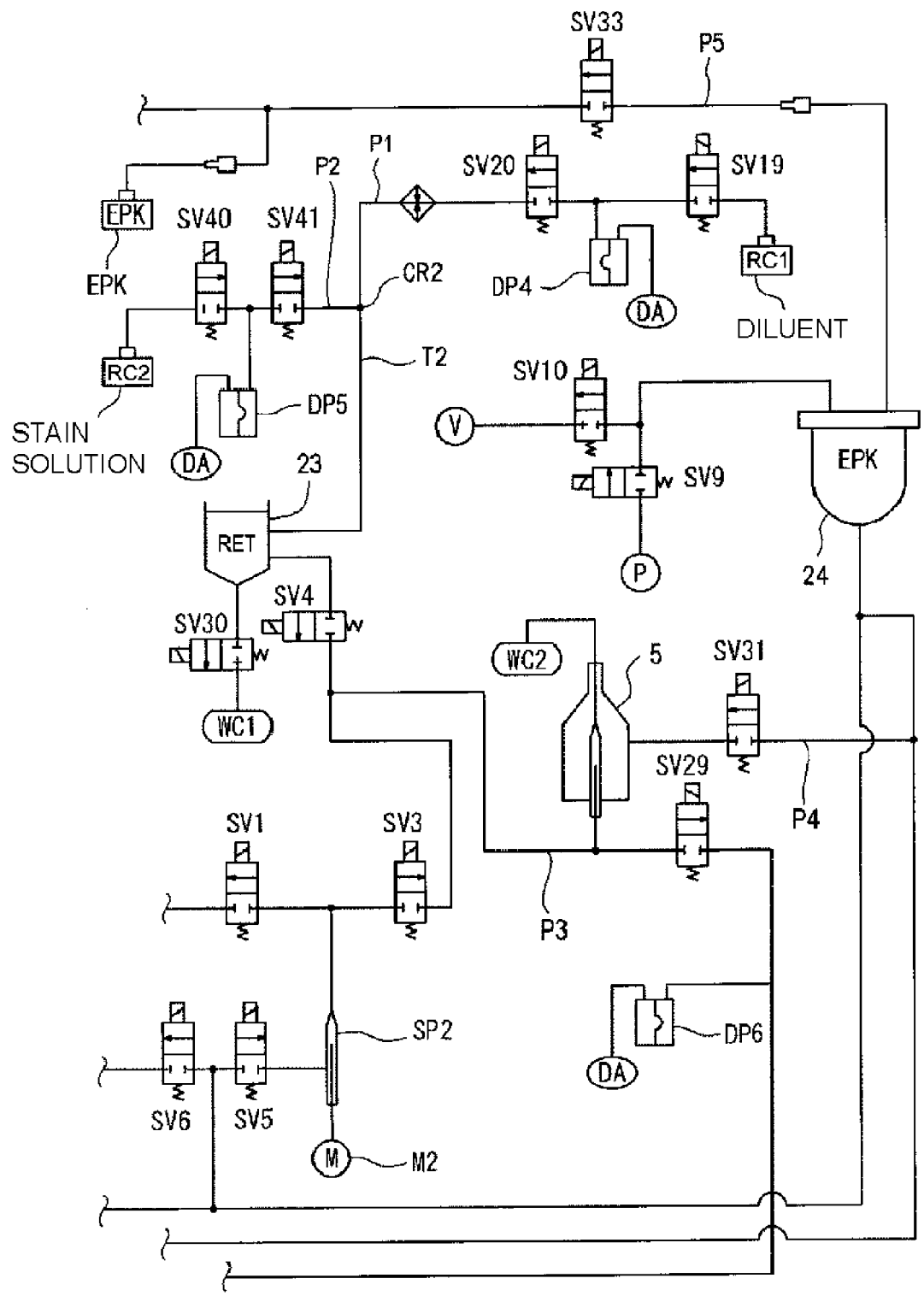
FIG. 6 is a fluid circuit diagram showing a specimen preparation section of the measurement unit according to the embodiment.

FIG. 5 is a block diagram showing a configuration of the measurement unit 2. FIG. 6 is a fluid circuit diagram showing a configuration of the specimen preparation section 4. As shown in FIG. 5, the measurement unit 2 includes the specimen preparation section 4, an RET detector 5, an RBC detector 6, an HGB detector 7, a controller 8, and a communication section 9.

The controller 8 includes a CPU, a ROM, a RAM, and the like, and controls the operation of each component of the measurement unit 2. The communication section 9 is, for example, an RS-232C interface, a USB interface, or an Ethernet (registered trademark) interface, and transmits/receives data to/from the data processing unit 3.

As shown in FIG. 6, the specimen preparation section 4 is a fluid unit that includes the chambers, a plurality of solenoid valves, diaphragm pumps, and the like. The chamber 22 is used for preparing a specimen that is used for measuring red blood cells, platelets, and hemoglobin. The chamber 23 is used for preparing a specimen that is used for measuring reticulocytes. Note that, in order to simplify the description, FIG. 6 only shows a part of the configuration of the fluid circuit, the part being in the vicinity of the chamber 23.

The chamber 23 is connected to a reagent container RC1 that contains a diluent containing a hemolytic agent and to a reagent container RC2 that contains a stain solution, via fluid flow paths P1 and P2 that are tubes, for example. Along the fluid flow path P1 connecting the chamber 23 and the reagent container RC1, solenoid valves SV19 and SV20 are provided. Also, a diaphragm pump DP4 is provided between the solenoid valves SV19 and SV20. The diaphragm pump DP4 is connected to a positive pressure source and a negative pressure source so that the diaphragm pump DP4 can be driven by positive pressure and negative pressure. Further, along the fluid flow path P2 connecting the chamber 23 and the reagent container RC2, solenoid valves SV40 and SV41 are provided. A diaphragm pump DP5 is provided between the solenoid valves SV40 and SV41.

The controller 8 controls these solenoid valves SV19, SV20, SV40, SV41, and the diaphragm pumps DP4 and DP5 in a manner described below, thereby supplying the diluent containing the hemolytic agent and the stain solution to the chamber 23.

First, the solenoid valve SV19, which is provided closer to the reagent container RC1 than the diaphragm pump DP4, is opened, and the diaphragm pump DP4 is driven by negative pressure while the solenoid valve SV20, which is provided closer to the chamber 23 than the diaphragm pump DP4, is kept closed. As a result, a fixed quantity of the diluent is taken from the reagent container RC1. Thereafter, the solenoid valve SV19 is closed and the solenoid valve SV20 is opened, and the diaphragm pump DP4 is driven by positive pressure, whereby the diluent of the fixed quantity is supplied to the chamber 23.

Similarly, the solenoid valve SV40, which is provided closer to the reagent container RC2 than the diaphragm pump DP5, is opened. Then, the diaphragm pump DP5 is driven by negative pressure while the solenoid valve SV41, which is provided closer to the chamber 23 than the diaphragm pump DP5, is kept closed. As a result, a fixed quantity of the stain solution is taken from the reagent container RC2. Thereafter, the solenoid valve SV40 is closed and the solenoid valve SV41 is opened, and the diaphragm pump DP5 is driven by positive pressure, whereby the stain solution of the fixed quantity is supplied to the chamber 23. In this manner, the blood specimen and the reagents (the diluent and the stain solution) are mixed and thereby a specimen to be used for measurement of reticulocytes is prepared.

The chamber 23 is connected to the RET detector 5 that is a flow cytometer, via a fluid flow path P3 that includes a tube and a solenoid valve SV4. The fluid flow path P3 has a branch, and solenoid valves SV1 and SV3 are serially connected to the branch path. A syringe pump SP2 is provided between the solenoid valves SV1 and SV3. A stepping motor M2 is connected to the syringe pump SP2. The syringe pump SP2 is driven through the operation of the stepping motor M2.

The fluid flow path P3 connecting the chamber 23 and the RET detector 5 has another branch, and a solenoid valve SV29 and a diaphragm pump DP6 are connected to this other branch. In the case of measuring reticulocytes by using the RET detector 5, the diaphragm pump DP6 is driven by negative pressure while the solenoid valves SV4 and SV29 are kept open, and the specimen is aspirated from the chamber 23. In this manner, the fluid flow path P3 is charged with the specimen. When the charging of the specimen is completed, the solenoid valves SV4 and SV29 are closed. Thereafter, the solenoid valve SV3 is opened and the syringe pump SP2 is driven, whereby the charged specimen is supplied to the RET detector 5.

As shown in FIG. 6, the specimen preparation section 4 is provided with a sheath liquid chamber 24. The sheath liquid chamber 24 is connected to the RET detector 5 via a fluid flow path P4. The fluid flow path P4 is provided with a solenoid valve SV31. The sheath liquid chamber 24 is provided for storing a sheath liquid to be supplied to the RET detector 5. The sheath liquid chamber 24 is connected to a sheath liquid container EPK containing the sheath liquid, via a fluid flow path P5 that includes a tube and a solenoid valve SV33. Note that the diluent contained in the reagent container RC1 may be used as the sheath liquid.

Before the measurement of reticulocytes starts, the solenoid valve SV33 is opened and the sheath liquid is supplied to the sheath liquid chamber 24. In this manner, the sheath liquid is stored in the sheath liquid chamber 24 in advance. At the start of the measurement of reticulocytes, a solenoid valve SV31 is opened in synchronization with the aforementioned supplying of the specimen to the RET detector 5, and thereby the sheath liquid stored in the sheath liquid chamber 24 is supplied to the RET detector 5.

The RET detector 5 is an optical flow cytometer that is capable of measuring reticulocytes by flow cytometry using a semiconductor laser. The RET detector 5 includes a flow cell 51 for forming a liquid flow of the specimen.

Figure 7:
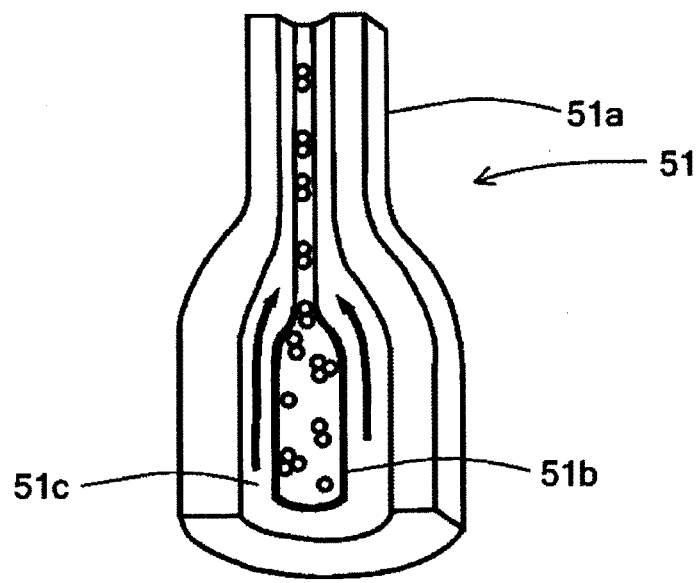
FIG. 7 is a perspective view schematically showing a configuration of a flow cell according to the embodiment.

FIG. 7 is a perspective view schematically showing a configuration of the flow cell 51. The flow cell 51 is formed from a translucent material such as quartz, glass, synthetic resin or the like, and has a tubular shape. The flow cell 51 has a flow path therein, through which the specimen and the sheath liquid flow. The flow cell 51 is provided with an orifice 51a, at which the inner space of the flow cell 51 is narrower than the inner space of the other parts of the flow cell 51. The flow cell 51 has a double-tube structure in the vicinity of the entrance of the orifice 51a. The inner tube portion thereof serves as a specimen nozzle 51b. The specimen nozzle 51b is connected to the fluid flow path P3 of the specimen preparation section 4. The specimen is discharged from the specimen nozzle 51b to the orifice 51a.

Space outside the specimen nozzle 51b serves as a flow path 51c through which the sheath liquid flows. The flow path 51c is connected to the aforementioned fluid flow path P4. The sheath liquid supplied from the sheath liquid chamber 24 flows through the fluid flow path P4 into the flow path 51c, and is then led to the orifice 51a. The sheath liquid supplied to the flow cell 51 in this manner flows so as to surround the specimen discharged from the specimen nozzle 51b. Then, the orifice 51a narrows down the stream of the specimen. As a result, particles contained in the specimen, such as reticulocytes and red blood cells, which are surrounded by the sheath liquid, pass through the orifice 51a one by one.

Figure 8:
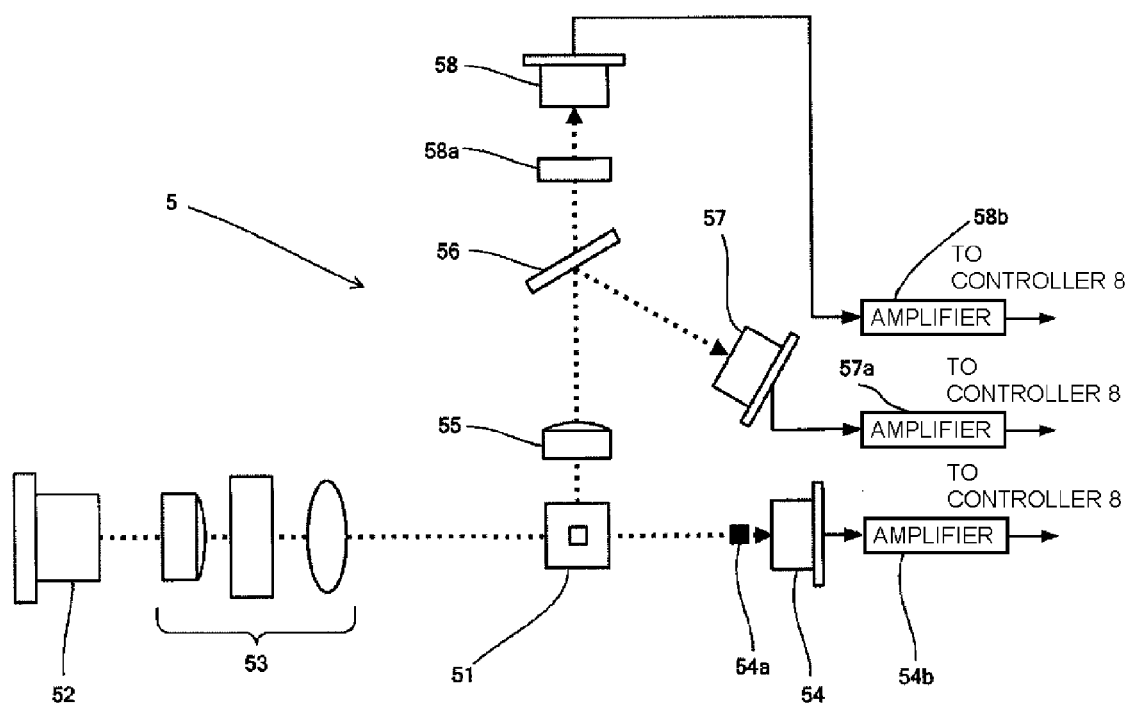
FIG. 8 schematically shows a configuration of a flow cytometer according to the embodiment.

FIG. 8 shows a schematic configuration of the RET detector 5. In the RET detector 5, a semiconductor laser light source 52 is disposed so as to output laser light to the orifice 51a of the flow cell 51. An illumination lens system 53 including a plurality of lenses is provided between the semiconductor laser light source 52 and the flow cell 51. The illumination lens system 53 focuses a parallel beam outputted from the semiconductor laser light source 52, to form a beam spot.

On an optical axis that linearly extends from the semiconductor laser light source 52, a beam stopper 54a is provided in an opposed position to the illumination lens system 53, with the flow cell 51 provided therebetween. Among laser beams outputted from the semiconductor laser light source 52, a beam that travels straight within the flow cell 51 without being scattered (hereinafter, referred to as "direct light") is blocked by the beam stopper 54a. Further, a photodiode 54 is provided on the optical axis so as to be located to the downstream side of the beam stopper 54a.

When the specimen flows into the flow cell 51, scattered light signals and fluorescence signals occur due to the laser light, among which forward light signals (scattered light signals) are emitted toward the photodiode 54. From among lights traveling along the optical axis that linearly extends from the semiconductor laser light source 52, the direct light from the semiconductor laser light source 52 is blocked by the beam stopper 54a. Incident on the photodiode 54 is only the scattered light that travels substantially along the optical axis direction (hereinafter, referred to as forward scattered light).

The forward scattered light emitted from the flow cell 51 is photoelectrically converted by the photodiode 54. Each electrical signal resulting from the photoelectric conversion (hereinafter, referred to as a forward scattered light signal) is amplified by an amplifier 54b and then outputted to the controller 8. The forward scattered light signal indicates a size of a blood cell. The forward scattered light signal is, after being processed by the controller 8, outputted to the data processing unit 3 via the communication section 9.

A side condenser lens 55 is provided laterally to the flow cell 51, so as to be located in a direction that is perpendicular to the optical axis that linearly extends from the semiconductor laser light source 52 to the photodiode 54. The side condenser lens 55 condenses side light that occurs when the semiconductor laser illuminates blood cells that are passing through the flow cell 51 (i.e., light that is outputted in the direction perpendicular to the optical axis). A dichroic mirror 56 is provided to the downstream side of the side condenser lens 55. Side light signals transmitted from the side condenser lens 55 are separated by the dichroic mirror 56 into scattered light components and fluorescence components.

A photodiode 57 for receiving side scattered light is provided laterally to the dichroic mirror 56 (i.e., provided in a direction that intersects an optical axis direction connecting the side condenser lens 55 and the dichroic mirror 56). Further, an optical filter 58a and an avalanche photodiode 58 are provided, on the optical axis, to the downstream side of the dichroic mirror 56.

Side scattered light components reflected by the dichroic mirror 56 are photoelectrically converted by the photodiode 57. Each electrical signal resulting from the photoelectric conversion (hereinafter, referred to as a side scattered light signal) is amplified by an amplifier 57a, and then outputted to the controller 8. The side scattered light signal indicates information about the inside of a blood cell (e.g., the size of the nucleus). The side scattered light signal is outputted to the data processing unit 3 via the communication section 9 after being processed by the controller 8.

Side fluorescence components transmitted through the dichroic mirror 56 are photoelectrically converted by the avalanche photodiode 58 after being wavelength-selected by the optical filter 58a. Each electrical signal resulting from the photoelectric conversion (a side fluorescence signal) is amplified by an amplifier 58b, and then outputted to the controller 8. The side fluorescence signal indicates information about the degree of staining of a blood cell. The side fluorescence signal is, after being processed by the controller 8, outputted to the data processing unit 3 via the communication section 9.

The RBC detector 6 is capable of measuring a red blood cell count and a platelet count by the sheath flow DC detection method. The RBC detector 6 has an electrical resistance detector. The aforementioned specimen is supplied from the chamber 22 to this detector. In the case of performing measurement on red blood cells and platelets, the specimen is prepared in the chamber 22 by mixing the blood with a diluent. The specimen is supplied from the specimen preparation section 4 to the detector, together with the sheath liquid. Within the detector, a liquid flow in which the specimen is surrounded by the sheath liquid is formed in the same manner as described above.

Along a flow path within the detector, an aperture having an electrode is provided. When blood cells contained in the specimen pass through the aperture one by one, a DC resistance at the aperture is detected, and an electrical signal corresponding to the DC resistance is outputted to the controller 8. The DC resistance increases when a blood cell passes through the aperture. Accordingly, the electrical signal is information indicating the passage of the blood cell through the aperture. The electrical signal is processed by the controller 8, and then transmitted to the data processing unit 3 via the communication section 9. The data processing unit 3 analyzes the received data to count red blood cells and platelets.

The HGB detector 7 is capable of measuring hemoglobin content by the SLS-hemoglobin method. The HGB detector 7 is provided with a cell for containing the diluted specimen. The specimen is supplied from the chamber 22 to the cell. In the case of measuring hemoglobin, the specimen is prepared in the chamber 22 by mixing the blood with a diluent and a hemolytic agent. The hemolytic agent has a property of converting hemoglobin in the blood to SLS-hemoglobin. A light-emitting diode and a photodiode are arranged so as to be opposed to each other with the cell located therebetween. Light from the light emitting diode is received by the photodiode.

The light-emitting diode emits light of a wavelength having a high rate of absorption by SLS-hemoglobin. The cell is formed from a plastic material having high translucency. As a result, the light emitted from the light-emitting diode is absorbed almost solely by the diluted specimen, and the transmitted light is received by the photodiode. The photodiode outputs an electrical signal corresponding to the amount of the received light (i.e., corresponding to an absorbance) to the controller 8. The absorbance and an absorbance obtained in advance by measuring only the diluent are subjected to signal processing by the controller 8, and then transmitted to the data processing unit 3 via the communication section 9. The data processing unit 3 compares the absorbances in the above two cases to calculate a hemoglobin value.

Figure 9:
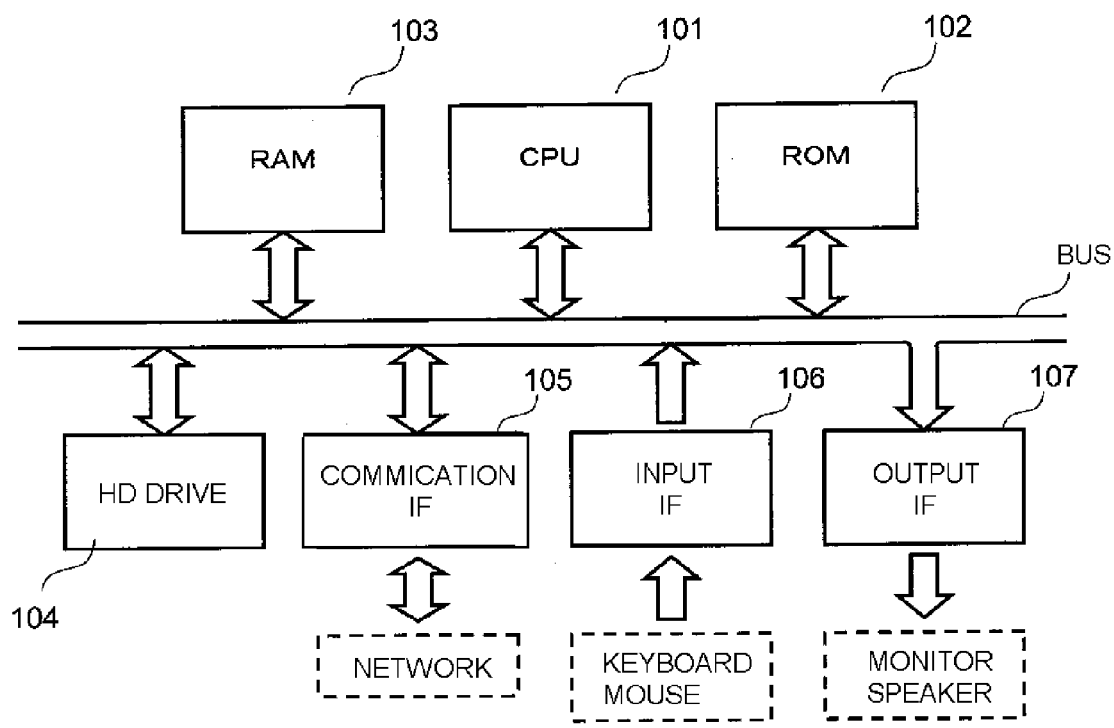
FIG. 9 is a block diagram showing a configuration of a data processing unit according to the embodiment.

FIG. 9 is a block diagram showing a configuration of the data processing unit 3. The data processing unit 3 is structured as a computer system that includes: a CPU 101; a ROM 102; a RAM 103; a hard disk drive (HD drive) 104; a communication interface 105; an input interface 106 including a keyboard, a mouse, and the like; and an output interface 107 including a monitor, a speaker, and the like.

For example, the communication interface 105 is an RS-232C interface, a USB interface, or an Ethernet (registered trademark) interface, and is capable of transmitting/receiving data to/from the measurement unit 2. Installed in a hard disk within the HD drive 104 are an operating system and an application program that is used for performing an analysis process on measurement data received from the measurement unit 2.

Through execution of the application program by the CPU 101, the analysis process is performed on the measurement data received from the measurement unit 2. As a result, a red blood cell count (RBC), hemoglobin content (HGB), hematocrit value (HCT), mean red blood cell volume (MCV), mean red blood cell hemoglobin (MCH), mean red blood cell hemoglobin concentration (MCHC), and a platelet count (PLT) are calculated. Further, a scattergram is created based on the forward scattered light signals and the side fluorescence signals, whereby the number of reticulocytes (RET) is counted.

Figure 10:
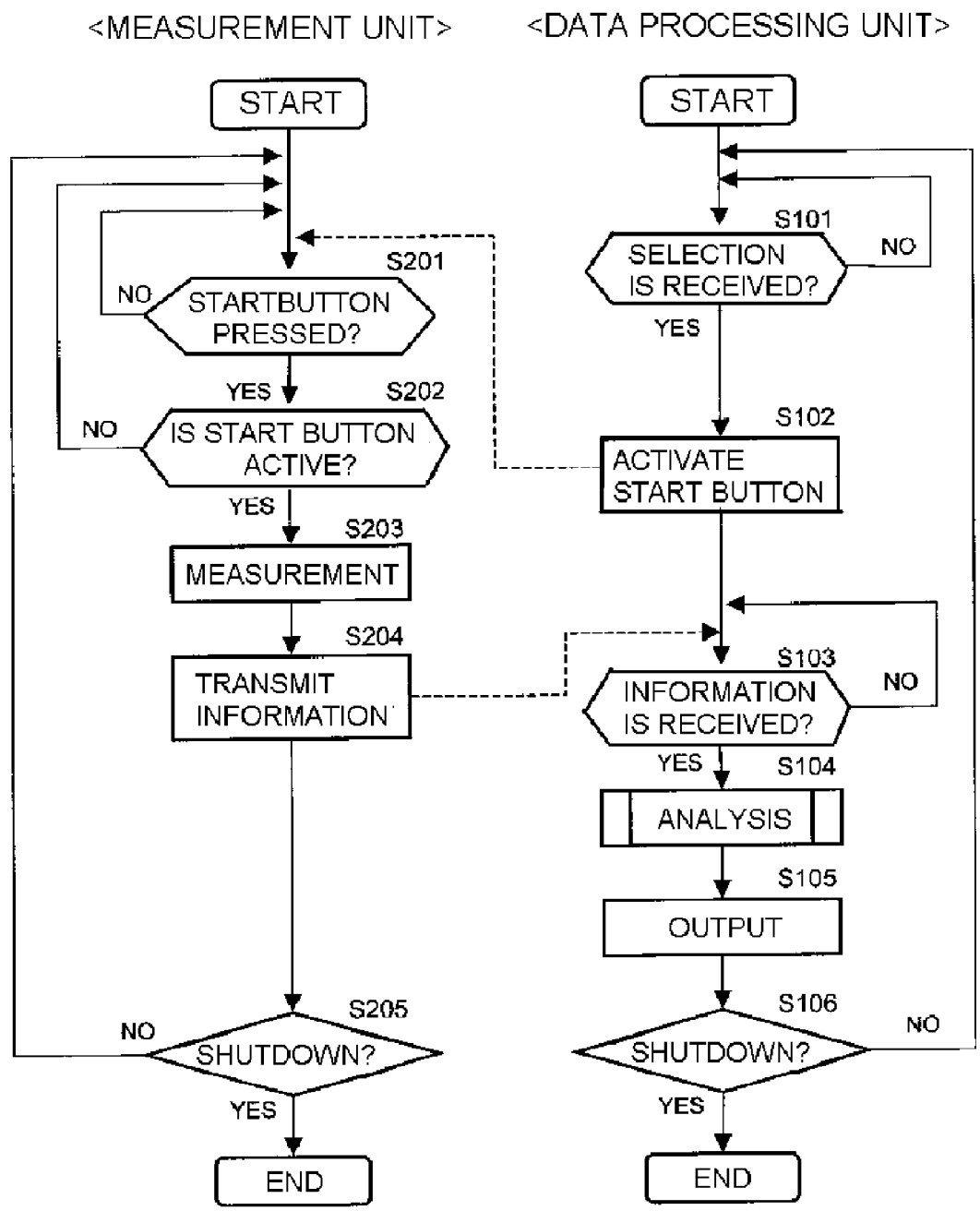
FIG. 10 is a flowchart of processing performed when reticulocytes are measured according to the embodiment.

FIG. 10 shows a flow of processing that is performed by the blood cell measuring apparatus according to the present embodiment when the blood cell measuring apparatus performs reticulocyte measurement. Note that the processing flow at the data processing unit 3 as shown in FIG. 10 is performed through execution, by the CPU 101 of the data processing unit 3, of the application program stored in the HD drive 104.

When a reticulocyte measurement mode is started, a reception screen for receiving the selection of an animal species is displayed on the monitor of the data processing unit 3 (S101). The reception screen includes icons indicating animal species options (feline, canine, etc).

When a user selects a desired animal species from among the displayed animal species by using a mouse (S101: YES), a signal for activating the start button 2c is transmitted to the measurement unit 2 (S102). Thereafter, the CPU 101 waits for data transmission from the measurement unit 2 (S103).

When the start button 2c is pressed (S201: YES), the measurement unit 2 determines whether or not the start button 2c is active (step S202). If the start button 2c is active (step S202: YES), the specimen is prepared in the chamber 23 as described above. The measurement unit 2 performs measurement at the RET detector 5 by using the prepared specimen, thereby obtaining the aforementioned forward scattered light signals and the side fluorescence signals (S203). Data that results from processing the obtained forward scattered light signals and the side fluorescence signals are transmitted to the data processing unit 3 (S204).

Upon receiving these data of the forward scattered light signals and the side fluorescence signals (S103: YES), the CPU 101 analyzes the data in a manner corresponding to the animal species selected at step S101, thereby obtaining the number of reticulocytes contained in the specimen (S104). Information about the obtained reticulocyte count is displayed on the monitor (S105). After the measurement and display of the reticulocytes have been performed for the animal species desired by the user, the processing returns, if the system is not shut down (S106: N0, S205: NO), to step S101 and step S201 at which the next measurement instruction from the user is awaited.

Figure 11:
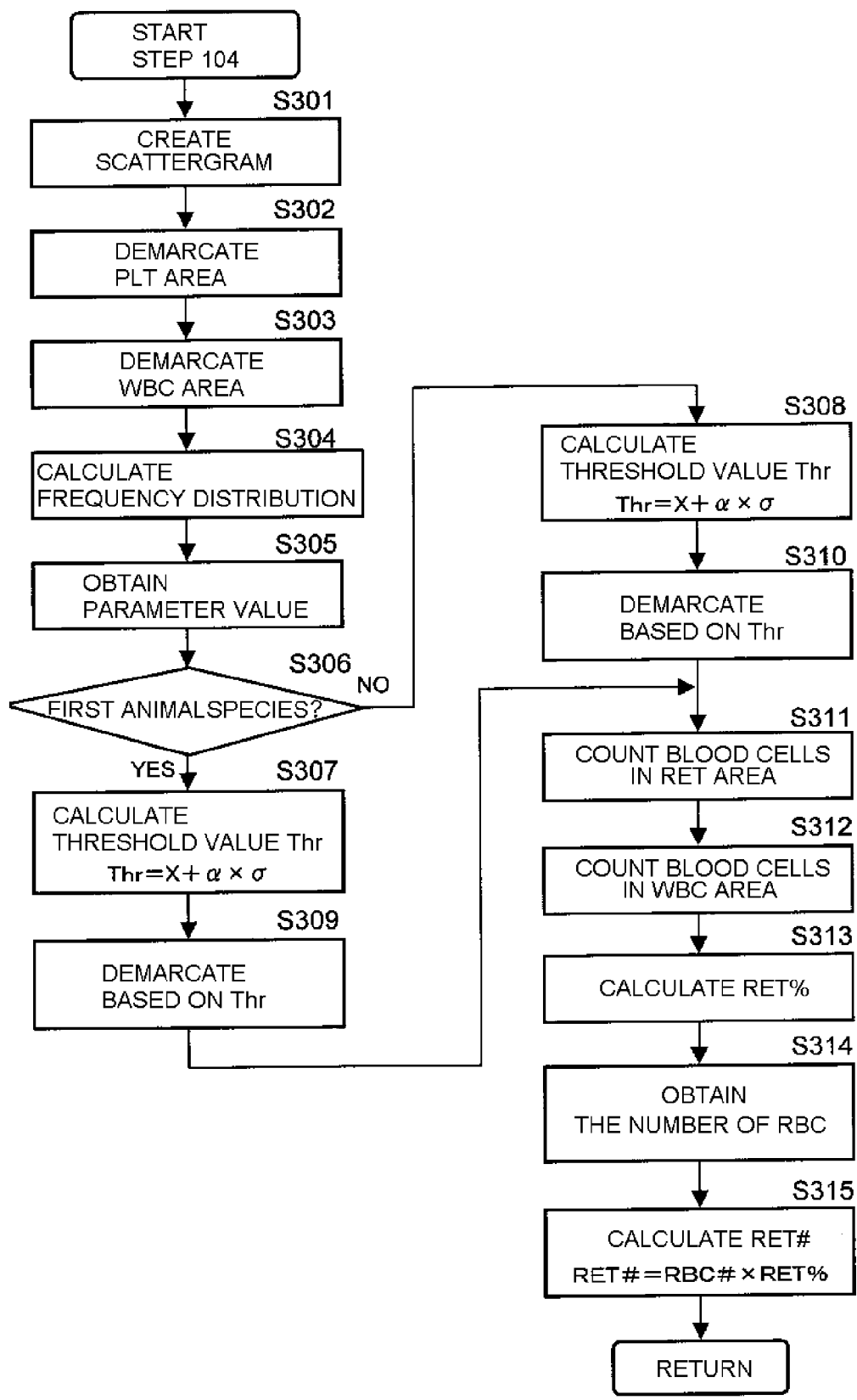
FIG. 11 is a flowchart showing a sub routine of an analysis process according to the embodiment.

FIG. 11 shows a process routine of the analysis process at step S104. FIGS. 12A to 14B show the manner of performing demarcation on a scattergram in the process routine. FIGS. 12A to 14A show an example of a scattergram in the case where feline blood is measured. FIG. 14B shows an example of a scattergram in the case where canine blood is measured. These scattergrams may be either two-dimensional scattergrams or three-dimensional scattergrams. For example, a two-dimensional scattergram is a distribution chart in which plot data, which indicate blood cells based on magnitudes of a parameter that is set as the vertical axis and based on magnitudes of a parameter that is set as the horizontal axis, are assigned to predetermined coordinates. Each set of coordinates is associated with values of plot data assigned thereto.

As described above, the analysis process at step S104 is performed in a manner corresponding to the animal species selected at step S101. When the animal species has been selected at step S101, demarcation conditions corresponding to the selected animal species (parameter values used for the demarcation) are set. In accordance with the demarcation conditions, demarcation is performed on a scattergram and reticulocytes are counted.

Figure 12A:
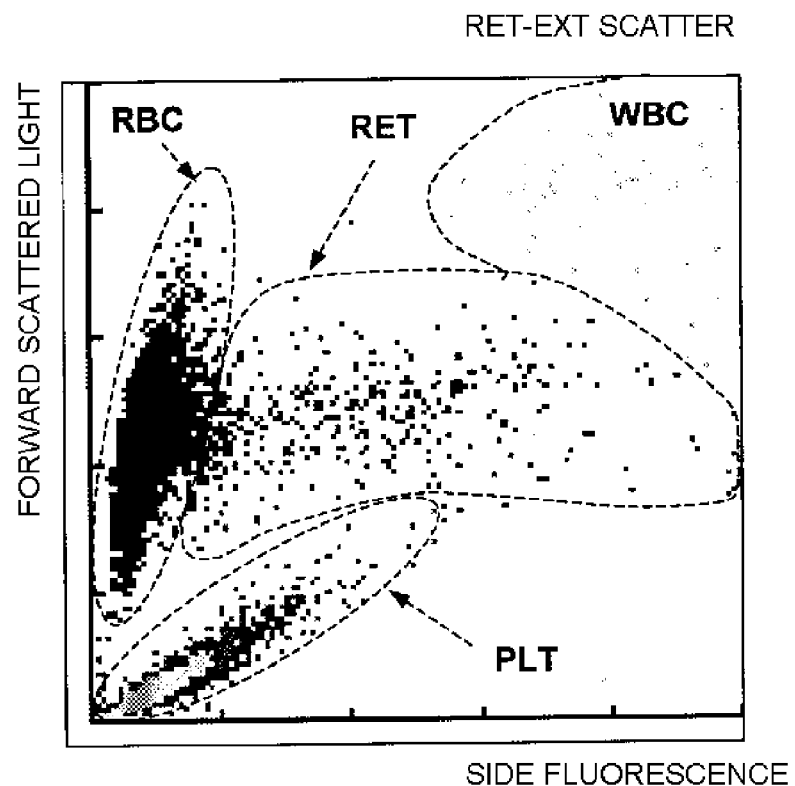
FIGS. 12A and 12B each show a scattergram illustrating the analysis process according to the embodiment.
Figure 12B:
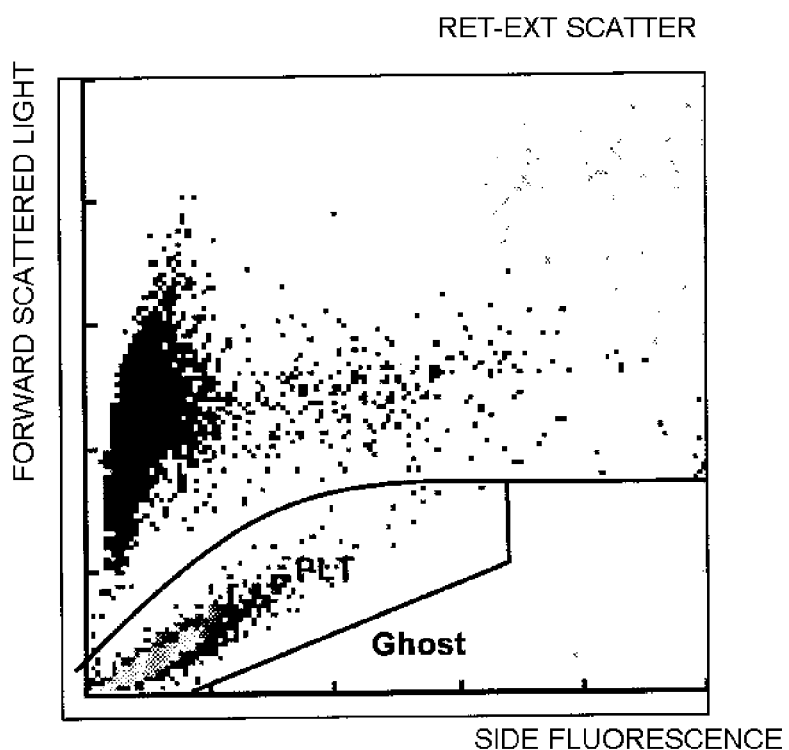

Upon receiving the data of the forward scattered light signals and the side fluorescence signals from the measurement unit 2, the CPU 101 first generates, at step S301, a scattergram whose vertical axis and horizontal axis represent the intensity of the forward scattered light and the intensity of the side fluorescence, respectively (see FIG. 12A). Next, at step S302, the CPU 101 demarcates a coordinate area of platelets (PLT) on the scattergram (see FIG. 12B), and also, demarcates a coordinate area of white blood cells (WBC) (see FIG. 13A). Here, demarcation of the coordinate area of white blood cells (WBC) is performed as described below.

Figure 13A:
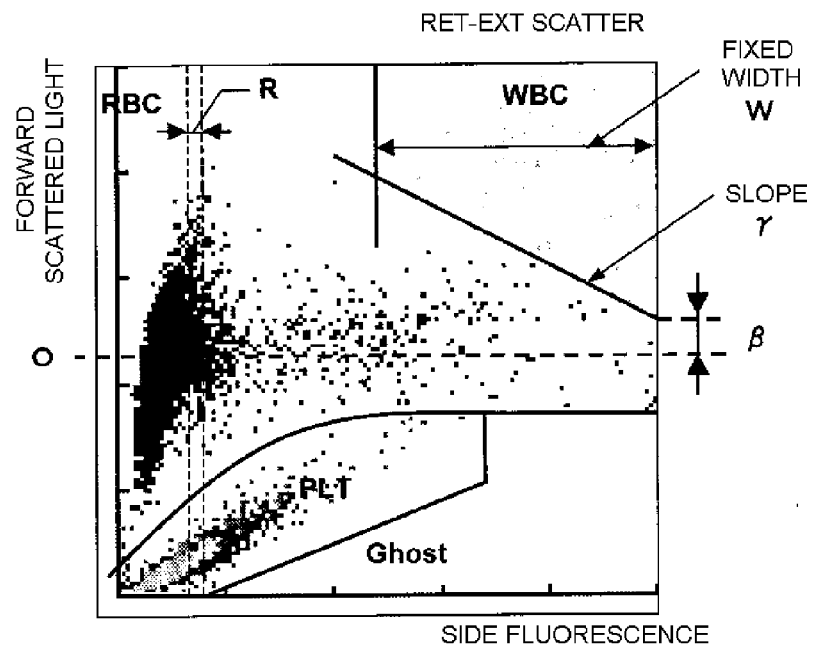
FIGS. 13A and 13B each show a demarcation process performed on the scattergram according to the embodiment.
Figure 14A:
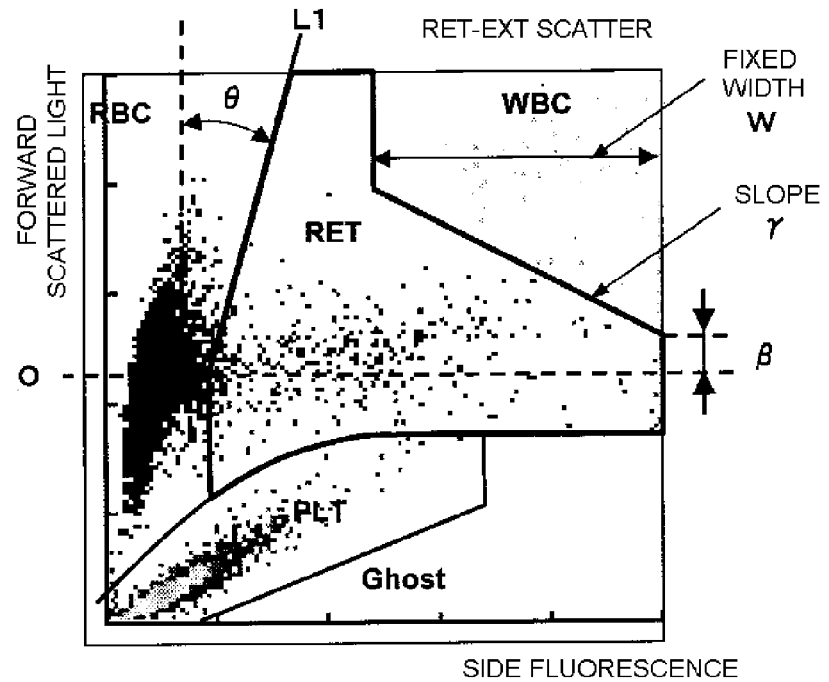
FIGS. 14A and 14B each show demarcation on the scattergram according to the embodiment.
Figure 14B:
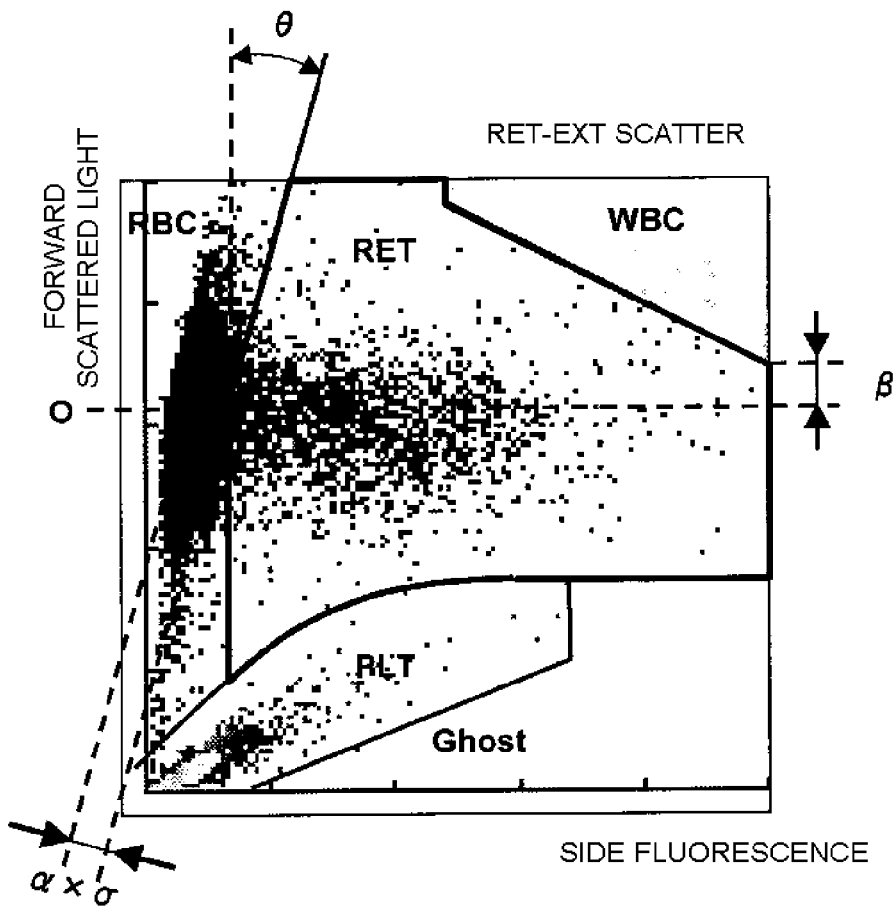

First, an axis O that passes through the centroid of a distribution of red blood cells (RBC) is set on the scattergram (see FIG. 13A). Here, the centroid of the distribution is set based on plot data present within a fixed area R that is set in advance around a coordinate area of the red blood cells (RBC). To be specific, a histogram in the vertical axis direction is obtained for the plot data present within the fixed area R. Then, the mean position of the histogram in the vertical axis direction is calculated. The mean position is set as the centroid of the distribution of red blood cells (RBC), and the axis O is set so as to extend through the centroid of the distribution and so as to be in parallel with the horizontal axis. A straight line with a slope $\gamma$ is drawn from a point that is shifted in the positive vertical axis direction by $\beta$ from an intersection point between the axis O set as above and a boundary indicating the maximum value of the side fluorescence intensity. An area, surrounded with the drawn straight line and a straight line that defines a fixed width W together with the boundary, is set as the coordinate area of white blood cells (WBC).

Figure 13B:
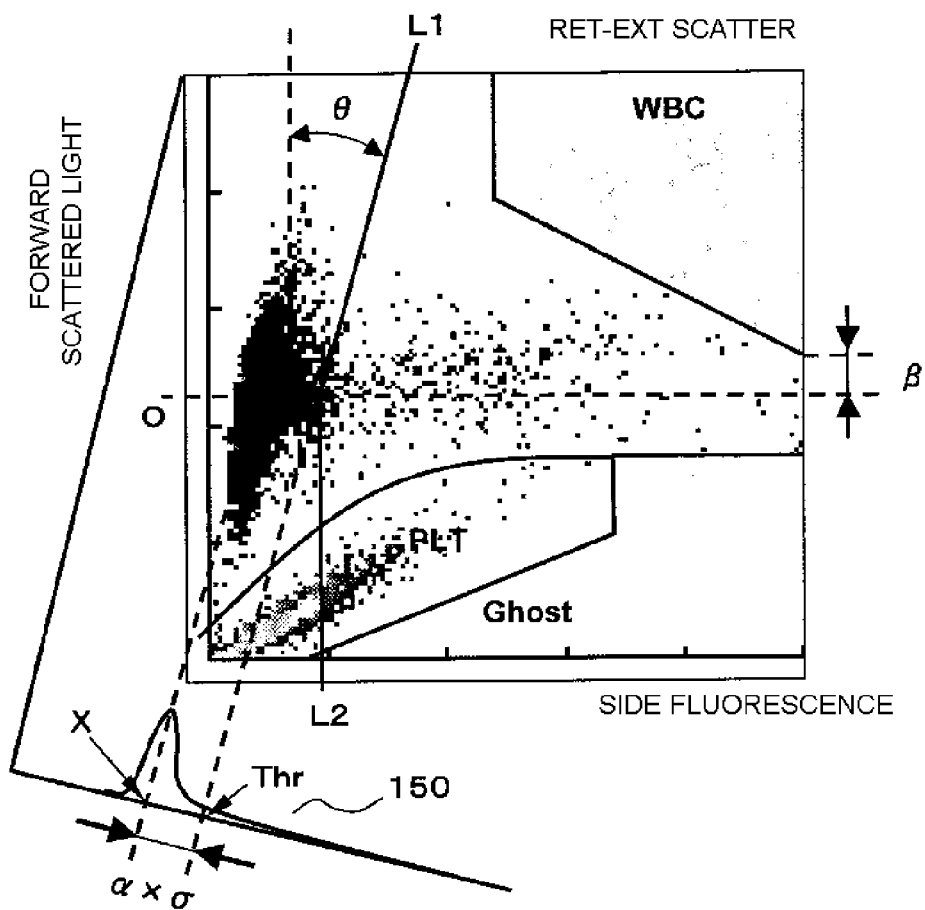

After the coordinate areas of platelets (PLT) and white blood cells (WBC) have been demarcated, the CPU 101 calculates, at step S304, a frequency distribution 150 of plot data with respect to the side fluorescence intensity, based on the scattergram from which these coordinate areas have been removed (see FIG. 13B).

Note that, in the example shown in FIG. 13B, plot data is projected onto an axis that is a result of rotating the horizontal axis of the scattergram by $\theta$ in the clockwise direction. In this manner, the frequency distribution 150 is calculated, with the rotated axis representing the side fluorescence intensity. This is because, as is understood from FIG. 13B, an area where a cluster of plot data of red blood cells (RBC) is present is an ellipsoidal area that is in a slightly rotated orientation in the clockwise direction. The rotation angle of the area where the cluster of plot data is present is variable depending on the reagents to be used in preparing the specimen. Depending on the reagents to be used, the area where the cluster of plot data of red blood cells (RBC) is present is not in such a rotated orientation but in the shape of an ellipse that is elongated in the vertical axis direction. Accordingly, when the frequency distribution is calculated, a rotation angle $\theta$ by which the axis representing the side fluorescence intensity is rotated is adjusted in accordance with the reagents to be used. Further, when the area where the cluster of plot data of red blood cells (RBC) is present is not in such a rotated orientation as above, the frequency distribution of plot data is calculated with respect to the horizontal axis of the scattergram.

When the frequency distribution has been calculated in this manner, the CPU 101 obtains at step S305, fluorescence intensity X that corresponds to a peak of the frequency distribution, and further calculates a variance $\sigma$ of the frequency distribution. Then, at step S306, the CPU 101 determines whether or not the animal species set by the user at step S101 of FIG. 10 is a first animal species (e.g., a "feline"). In the case of the first animal species (step S306: YES), the CPU 101 performs, at step S307, calculation based on the fluorescence intensity X, the variance $\sigma$, and a coefficient $\alpha$ corresponding to the first animal species (a "feline" in the example of FIGS. 12A to 14A), thereby calculating a threshold value Thr that indicates a border of aggregate reticulocytes (RET). The calculation is performed using the equation shown below.

$$Thr = X + \alpha \times \sigma \quad (1)$$

After the threshold value Thr has been calculated in the above manner, the CPU 101 demarcates, at step S309, a coordinate area of aggregate reticulocytes (RET) and a coordinate area of red blood cells (RBC) (the red blood cells including punctate reticulocytes (RET)), with a straight line L1 that is inclined by an angle $\theta$ with respect to the vertical axis of the scattergram and that passes through the threshold value Thr, and with a straight line L2 that extends downward, in parallel with the vertical axis, from an intersection point of the straight line L1 and the axis O (see FIG. 13B). In this manner, the coordinate area of aggregate reticulocytes (RET) is specified (see FIG. 14A). Thereafter, at step S311, the CPU 101 counts the number of plot data (the number of blood cells) contained in the coordinate area of aggregate reticulocytes (RET).

On the other hand, when the animal species set by the user at step S101 is not the first animal species (step S306: NO), the CPU 101 calculates, at step S308 based on the above equation (1), a threshold value Thr by using a coefficient $\alpha$ that corresponds to an animal species different from the first animal species. Then, the CPU 101 demarcates, at step S310, a coordinate area of reticulocytes (RET) (including both punctate reticulocytes and aggregate reticulocytes) and a coordinate area of red blood cells (RBC), with a straight line L1 that is inclined by the angle θ with respect to the vertical axis of the scattergram and that passes through the threshold value Thr, and with a straight line L2 that extends downward, in parallel with the vertical axis, from an intersection point of the straight line L1 and an axis O. In this manner, the coordinate area of reticulocytes (RET) is specified (see FIG. 14B). Subsequently, the CPU 101 counts, at step S311, the number of plot data (the number of blood cells) contained in the coordinate area of reticulocytes (RET).

In the case of an animal species different from the first animal species (e.g., a "canine"), the coefficient α in the above equation (1) is set to be ½ of the coefficient α in the case of a feline. The rotation angle θ, shift amount β, slope γ, and the fixed width W are the same for both the case of a feline and the case of a canine. As is understood from the comparison between FIG. 14A and FIG. 14B, the border between the coordinate area of red blood cells (RBC) and the coordinate area of reticulocytes (RET) in the case of a canine is, as compared to the case of a feline, shifted to the left in the scattergram. Based on such a difference between the borders, the coordinate area of aggregate reticulocytes is demarcated in the case of a feline, and the coordinate area containing all the reticulocytes (regardless of the difference between punctate reticulocytes and aggregate reticulocytes) is demarcated in the case of a canine.

Figure 15A:
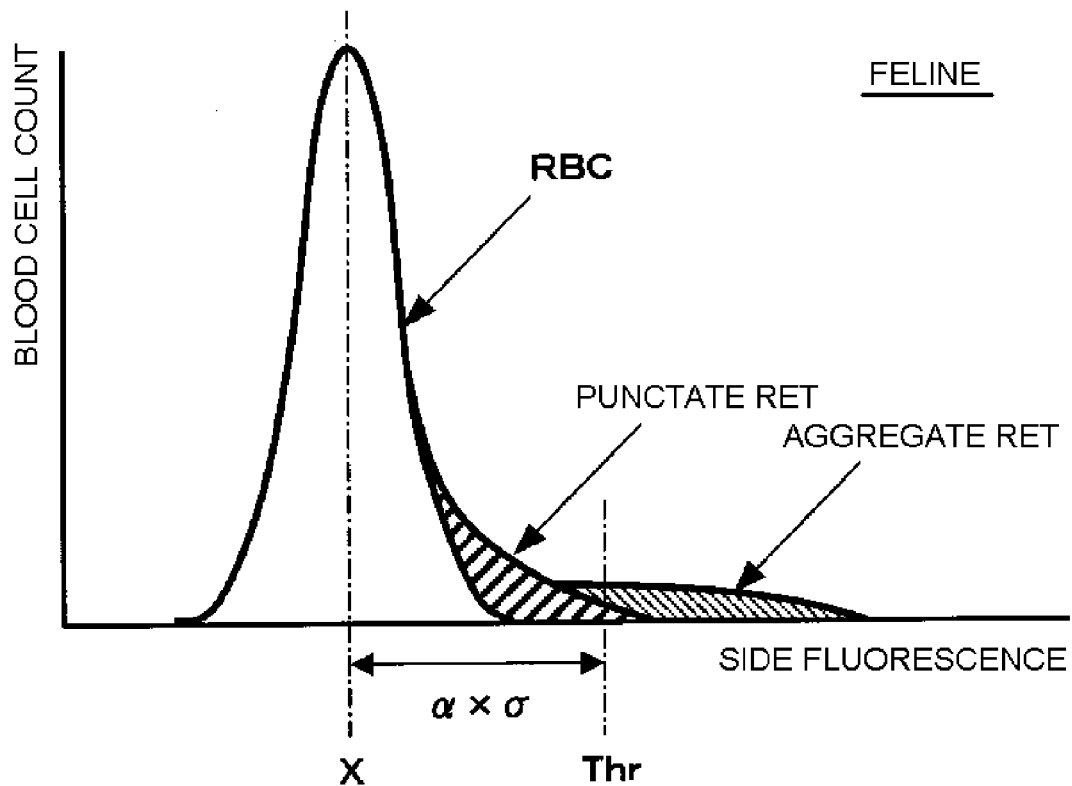
FIGS. 15A and 15B each schematically show the manner of setting a threshold value Thr according to the embodiment.
Figure 15B:
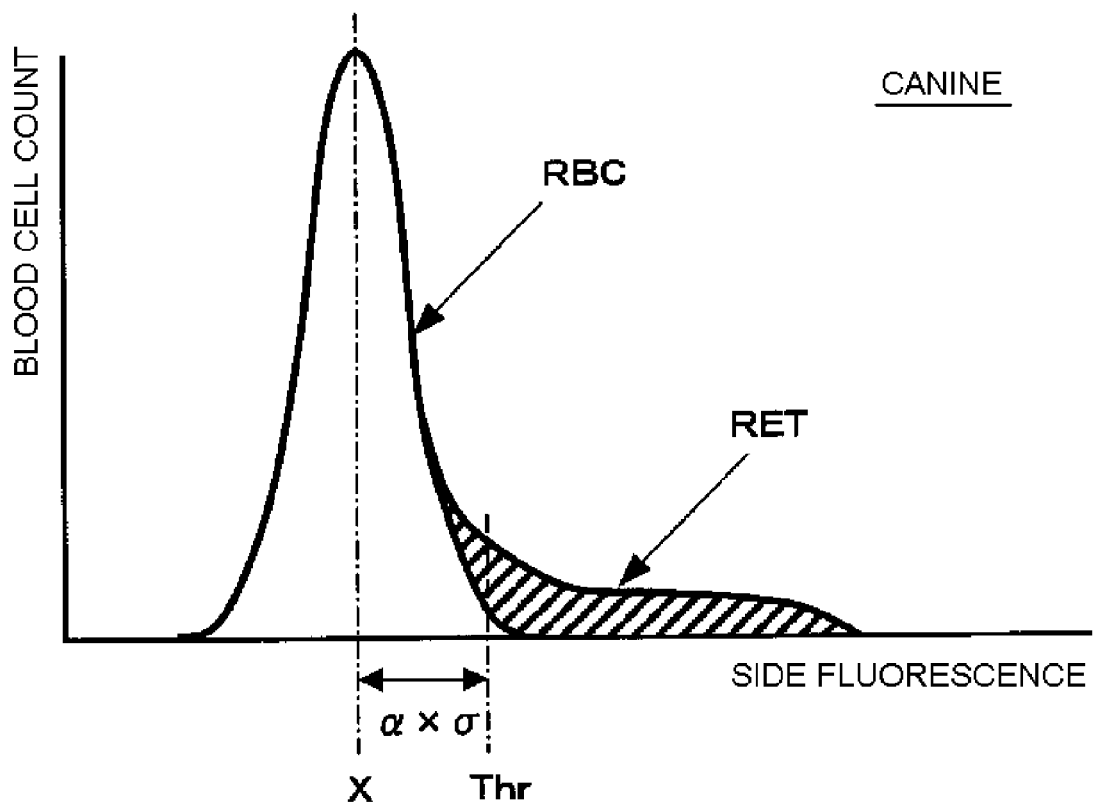

As described above, the coefficient α of the above equation (1) used at step S307 and step S308 is changed as necessary in accordance with the selected animal species. FIGS. 15A and 15B each schematically show, in the case where the plot data frequency distribution calculated at step S304 of FIG. 11 with respect to the side fluorescence intensity is divided based on blood cell types, the distribution of each type of blood cells. FIG. 15A is a distribution chart for feline blood, and FIG. 15B is a distribution chart for canine blood.

As shown in FIG. 15A, in the case of feline blood, a distribution of red blood cells (RBC), which is a normal distribution, is followed by a distribution of punctate reticulocytes (RET), which is followed by a distribution of aggregate reticulocytes (RET). Counting aggregate reticulocytes is considered to be useful when diagnosing animal species with anemia or the like, whose reticulocytes consist of a plurality of types of reticulocytes in the above manner. Therefore, in the case of feline blood, it is necessary to demarcate the coordinate area of reticulocytes (RET), with the threshold value Thr being set at the border position between the punctate reticulocytes and the aggregate reticulocytes.

On the other hand, in the case of canine blood, as shown in FIG. 15B, it is not necessary to distinguish between punctate reticulocytes and aggregate reticulocytes contained in the reticulocytes, but necessary to count the total number of reticulocytes (RET) that are distributed following the normally distributed red blood cells (RBC). Accordingly, in the case of canine blood, it is necessary to demarcate the coordinate area of reticulocytes (RET), with the threshold value Thr being set at the border position between the red blood cells (RBC) and the reticulocytes (RET).

As described above, the distribution of reticulocytes to be measured is different between the case of a canine and the case of a feline. For this reason, the coefficient α in the above equation (1) is required to be changed between the case of feline blood and the case of canine blood. It is at least necessary to set the coefficient α in the case of feline blood to be greater by a predetermined magnitude than that in the case of canine blood. To be specific, in the case of feline blood, the coefficient α is adjusted to be approximately the double of that in the case of canine blood.

After the blood cells in the RET coordinate area have been counted, the CPU 101 counts, at step S312, the number of plot data contained in the coordinate area of red blood cells (RBC), which has been demarcated at step S309 or step S310. Further, the CPU 101 calculates, at step S313, a proportion RET % that indicates a proportion of the number of reticulocytes to the counted number of red blood cells (RBC).

In parallel to the above process, the CPU 101 obtains, from the measurement unit 2 at step S314, information about the number of red blood cells (RBC), which has been obtained by the RBC detector 6 for the same blood. Further, at step S315, the CPU 101 obtains a count RET# that indicates the number of reticulocytes, by multiplying the obtained number of red blood cells (RBC) by the proportion RET %.

Here, the reticulocyte count RET# is obtained here by multiplying, by the proportion RET %, the number of red blood cells detected by the RBC detector 6. However, as an alternative, the number of reticulocytes (RET) obtained at step S311 can be used as the reticulocyte count RET#.

The reticulocyte proportion RET % and the reticulocyte count RET# measured in this manner are displayed on the monitor at step S105 of FIG. 10.

Described next are results that were obtained when measurement of aggregate reticulocytes (of a feline) was performed with the blood cell measuring apparatus according to the present embodiment (prototype).

Figure 16A:
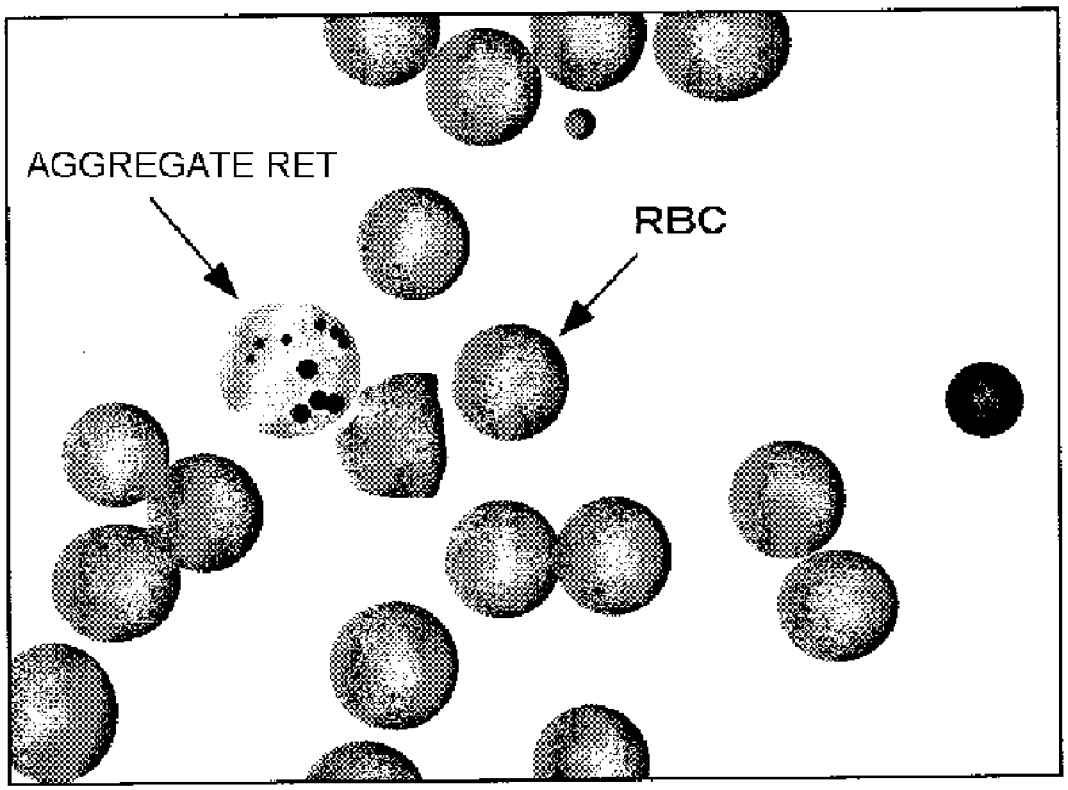
FIGS. 16A and 16B each schematically show a micrograph that shows an image of feline blood.
Figure 16B:
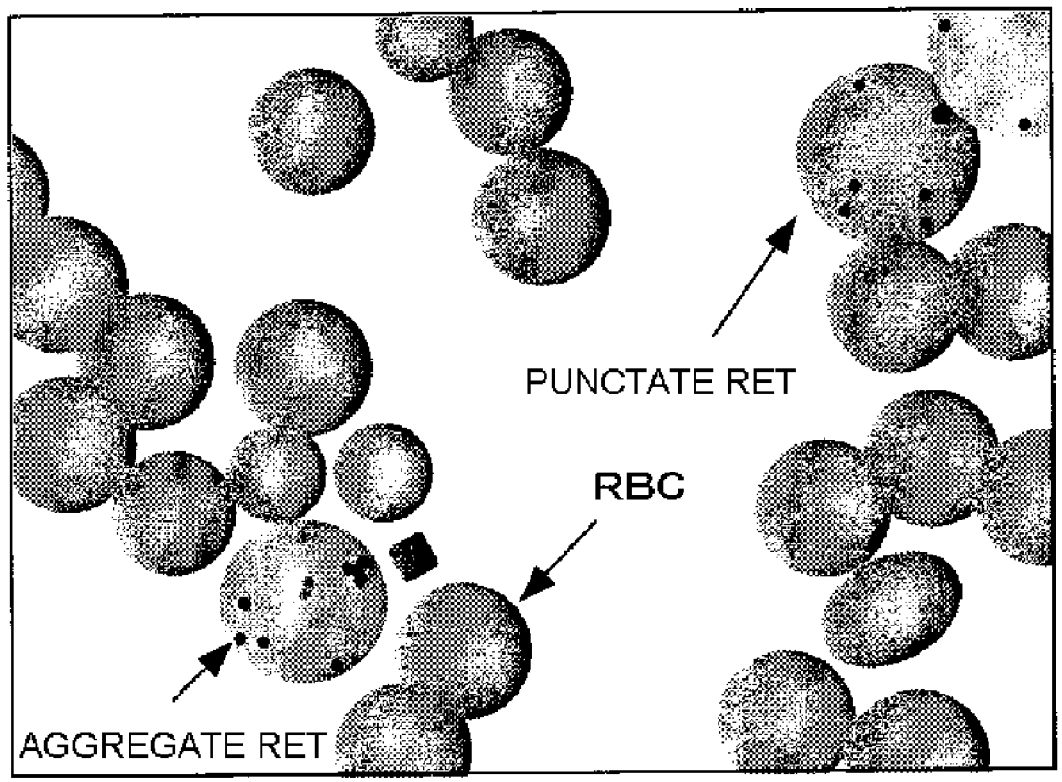

FIGS. 16A and 16B are schematic diagrams each showing a micrograph that shows feline blood. In each diagram, a blood cell that contains therein two or more granules (RNA) is a reticulocyte (RET). Among reticulocytes, those with granules aggregated therein are aggregate reticulocytes, and those with granules scattered therein are punctate reticulocytes.

In this measurement, measurement results of aggregate reticulocytes which were obtained when feline blood was measured by the blood cell measuring apparatus according to the present embodiment (prototype) were compared to measurement results of aggregate reticulocytes which were obtained when blood cells in the feline blood were visually measured with a microscope, whereby measurement accuracy of the blood cell measuring apparatus according to the present embodiment was verified. Each measurement was performed on 47 samples. Mean values of results of measurement performed by multiple persons are shown as the results of the visual measurement. The measurement by the blood cell measuring apparatus (prototype) was performed in accordance with the processing described above with reference to FIGS. 11 to 14B. Parameter values used for demarcation on a scattergram were set to those used for measurement of feline blood. The coefficient α in the above equation (1) was set to α=10 (double the coefficient α in the case of human or canines).

Figure 17A:
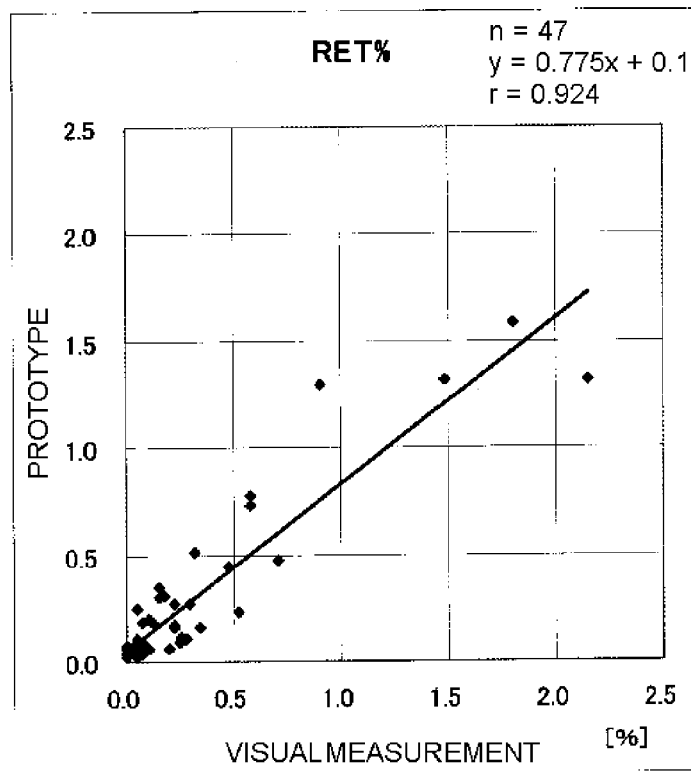
FIGS. 17A and 17B each show an example of verification of the blood cell measuring apparatus according to the embodiment.
Figure 17B:
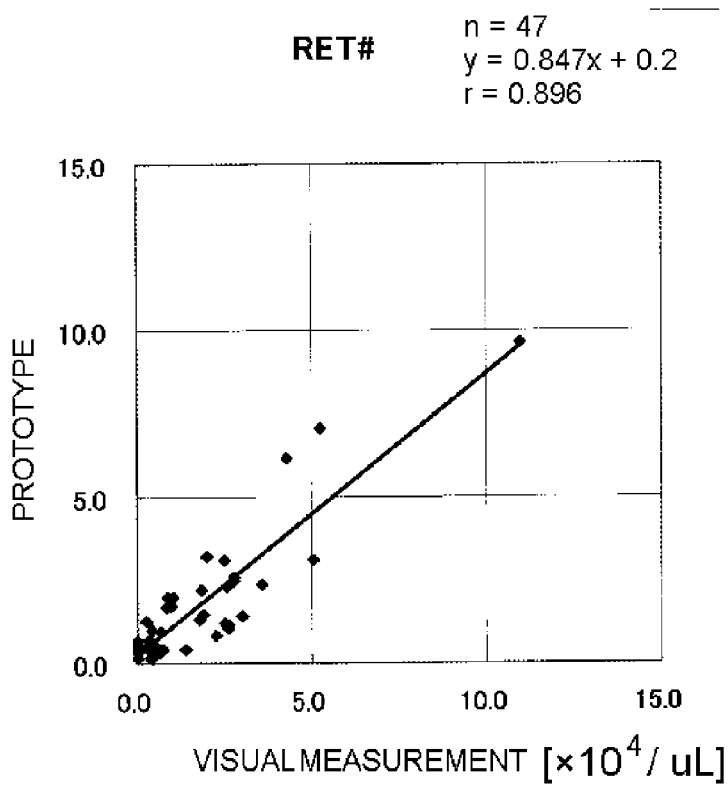

FIGS. 17A and 17B show the measurement results. In FIGS. 17A and 17B, the vertical axis represents values obtained by the prototype apparatus and the horizontal axis represents values obtained by the visual measurement. Each single point plotted on these diagrams represents, for the same sample, both a measurement result obtained by the prototype apparatus and a measurement result obtained by the visual measurement. In each diagram, a straight line that approximates all the plotted points therein is calculated, whereby a correlation between the measurement results of the prototype apparatus and the results of the visual measurement is obtained.

FIG. 17A shows, as measurement results, points each representing a proportion RET % that indicates a proportion of aggregate reticulocytes to the number of red blood cells. FIG. 17B shows, as measurement results, points each representing a count RET# that indicates the number of aggregate reticulocytes. Note that the count RET# was, similarly to the above-described manner, calculated by multiplying the number of red blood cells (a measurement result obtained by the RBC detector 6 of FIG. 5), which had been obtained based on a change in the electrical resistance value, by the proportion RET % calculated as shown in FIG. 17A.

A correlation r between the measurement results of the prototype apparatus and the results of the visual measurement, which is shown in FIG. 17A, and a correlation r between the measurement results of the prototype apparatus and the results of the visual measurement, which is shown in FIG. 17B, are r=0.924 and r=0.896, respectively. Thus, there is a substantially high correlation between the measurement results obtained by the prototype apparatus and the results obtained by the visual measurement. From these measurement results, measurement accuracy of the blood cell measuring apparatus according to the present embodiment (prototype) was verified to be sufficiently high when used in measurement of feline blood.

As described above, according to the present embodiment, the number of aggregate reticulocytes can be counted accurately. Since the number of aggregate reticulocytes can be counted without depending on visual measurement, a burden on veterinarians and laboratory technicians can be reduced substantially.

Further, in the present embodiment, an animal species to be measured can be selected as necessary. Therefore, not only the number of aggregate reticulocytes of such animal species as felines, but also the total number of reticulocytes of other animal species such as canines, can be measured. To be specific, when a feline is selected as an animal species to be measured, information about the number of aggregate reticulocytes (RET %, RET#) is outputted, and when a canine is selected as an animal species to be measured, information about the total number of reticulocytes (RET %, RET#) is outputted. Accordingly, veterinarians or laboratory technicians are only required to select an animal species to be measured, in order to obtain information about the number of reticulocytes, which is useful for making a diagnosis on the animal species. This substantially reduces their burden in making the diagnosis.

Although the above embodiment takes felines and canines as animal species to be measured, measurement can be performed on other animal species, of course. In such a case, if there exists, other than felines, animal species whose reticulocytes may contain aggregate reticulocytes, the coefficient $\alpha$ in the equation (1) is adjusted for the animal species, and the aggregate reticulocytes are measured, accordingly. Animal species whose reticulocytes may contain aggregate reticulocytes are, for example, rabbits, ferrets, etc.

In the above embodiment, the number of aggregate reticulocytes is measured and displayed in the case of the first animal species (a feline). Here, the number of punctate reticulocytes may be additionally measured and displayed. Alternatively, the total number of reticulocytes may be measured and displayed. Further, in the case of the first animal species (a feline), the user may select as necessary whether to measure and display only the number of aggregate reticulocytes, or to measure and display the number of punctate reticulocytes in addition to the number of aggregate reticulocytes, or to measure and display the total number of reticulocytes in addition to the number of aggregate reticulocytes.

Still further, the above embodiment measures aggregate reticulocytes when the first animal species is selected, and measures all the reticulocytes when the second animal species is selected. However, the present invention is not limited thereto. For example, when the first animal species is selected, punctate reticulocytes may be measured, and when the second animal species is selected, all the reticulocytes may be measured. Alternatively, when the first animal species is selected, aggregate reticulocytes may be measured, and when the second animal species is selected, punctate reticulocytes may be measured. Further alternatively, when the first animal species is selected, punctate reticulocytes may be measured, and when the second animal species is selected, aggregate reticulocytes may be measured.

Figure 18:
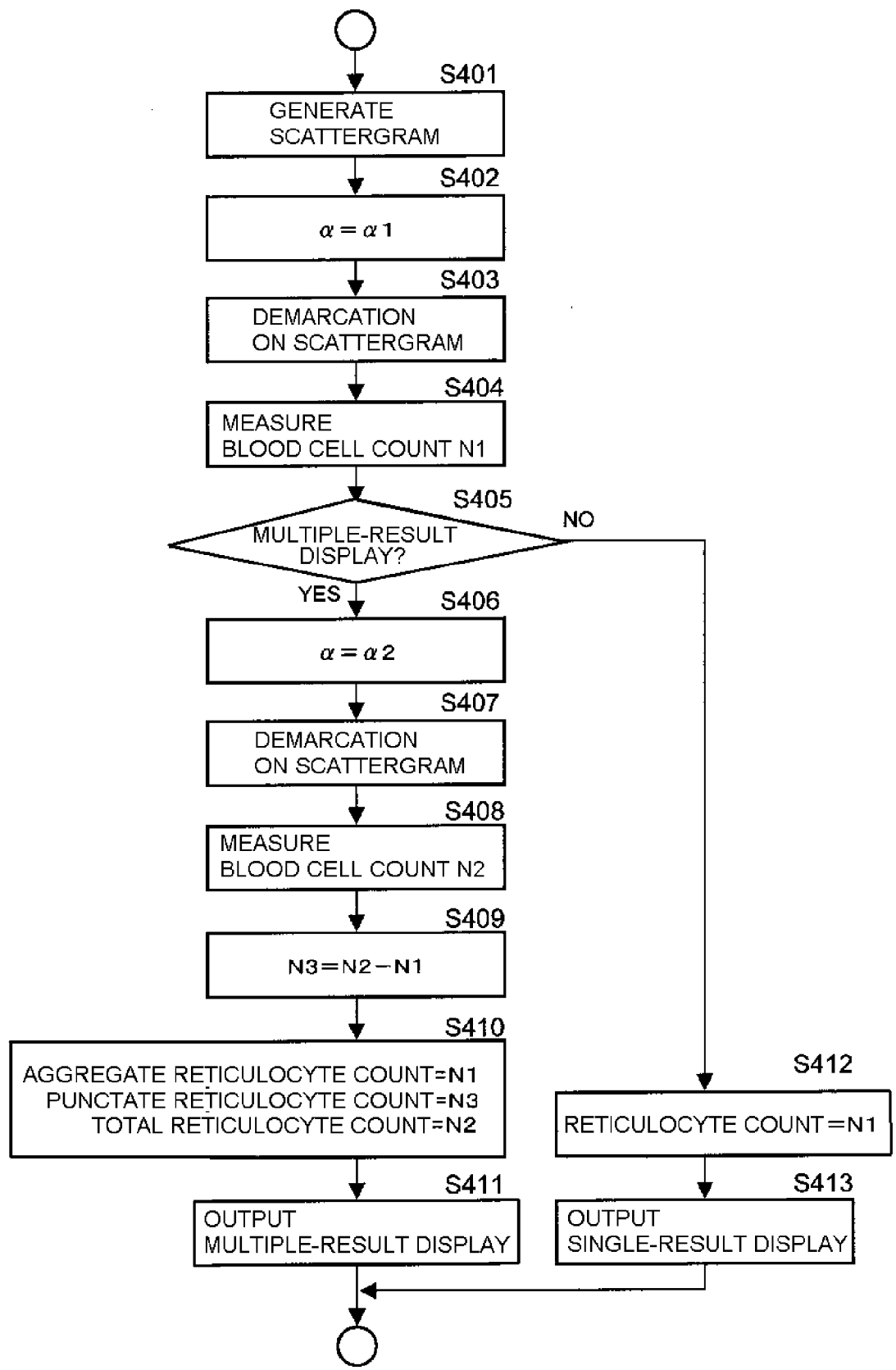
FIG. 18 is a flowchart showing a variation of an analysis routine according to the embodiment.

FIG. 18 shows a flow of processing that is performed when the number of punctate reticulocytes and the total number of reticulocytes are counted and displayed in addition to the number of aggregate reticulocytes, for the first animal species (e.g. a feline). In this processing flow, similarly to the above embodiment, a scattergram is created (S401), and the coefficient $\alpha$ of the above equation (1) is set to a coefficient $\alpha 1$ that is used for measuring aggregate reticulocytes (S402). Then, similarly to the above embodiment, a coordinate area of aggregate reticulocytes is demarcated using the coefficient $\alpha 1$ (S403), and a count N1 indicating the number of aggregate reticulocytes is measured (S404).

Here, when the user has not selected a multiple-result display (S405: NO), the number of reticulocytes to be displayed is, similarly to the above embodiment, regarded as the count N1 which has been measured at step S404 (S412). Then, a display output is performed based on the count N1 (S413).

On the other hand, when the user has selected a multiple-result display (C405: YES), the coefficient $\alpha$ of the above equation (1) is set to a coefficient $\alpha 2$ that is used for counting the total number of reticulocytes (including all the types of reticulocytes (e.g., both punctate and aggregate reticulocytes)) (S406). Then, the coefficient $\alpha 2$ is used, similarly to the above embodiment, to demarcate a coordinate area of reticulocytes (including all the types of reticulocytes (e.g., both punctate and aggregate reticulocytes)) (S407), and a count N2 indicating the total number of reticulocytes is measured (S408). Further, calculation N2−N1 is performed, whereby a count N3 indicating the number of punctate reticulocytes is calculated.

The counts N1, N2, and N3 obtained in the above manner are set as an aggregate reticulocyte count, a total reticulocyte count, and a punctate reticulocyte count, respectively (S410). Then, similarly to the above embodiment, a display output (RET %, RET#) based on each blood cell count is performed (S411). Note that when the user has selected only a display of the total number of reticulocytes in addition to a display of measurement results of aggregate reticulocytes, a display is performed for the number of aggregate reticulocytes and the total number of reticulocytes. In this case, step S409 of FIG. 18 is skipped. Further, when the user has selected only a display of measurement results of aggregate and punctate reticulocytes, a display is performed for the aggregate and punctate reticulocytes.

The embodiment of the present invention has been described as above. However, the present invention is not limited by the above embodiment in any way. Other than the foregoing description, numerous modifications of the embodiment of the present invention may be devised.

For example, the above embodiment generates a scattergram based on the intensity of the forward scattered light and the intensity of the side fluorescence, for the measurement of aggregate reticulocytes. Alternatively, aggregate reticulocytes may be measured based on the intensity of the side scattered light and the intensity of the side fluorescence, for example. Further alternatively, aggregate reticulocytes may be measured based on a plurality of types of fluorescence that are generated through illumination of laser light of a specific wavelength.

Further, FIGS. 12A to 14B referred to in the above embodiment indicate a feline as an example of the first animal species whose reticulocytes contain aggregate reticulocytes, and indicate a canine as an example of the second animal species whose reticulocytes do not contain aggregate reticulocytes. However, the first and second animal species may include different animal species other than felines and canines. The present invention can be applied, as necessary, to a blood cell measuring apparatus that performs measurement on animal species different from felines and canines.

Although the above embodiment displays both RET % and RET#, only either one of these may be displayed, alternatively. Further, other than the above information, different information based on the number of aggregate reticulocytes may be displayed.

Note that, in the measurement example of the above embodiment, the coefficient α of the above equation (1) in the case of measuring feline blood is set to be the double of that in the case of animal species whose reticulocytes do not contain aggregate reticulocytes (human or canines). However, the coefficient α here may not necessarily be the double of that in the case of human or canines, so long as the coefficient α is set to an appropriate value that is close to the double of the coefficient α used in the case of human or canines. The term "double" recited in claim 12 covers a range that is slightly greater and slightly less than the value that is double the coefficient α used in the case of human or canines.

Other than the above-described embodiment, various modifications can be devised as necessary without departing from the scope of the technical idea described in the claims.

What is claimed is:

1. An animal blood cell measuring apparatus comprising:
    a specimen preparation section for preparing a measurement specimen from blood of an animal and a stain solution;
    a characteristic information obtaining section which comprises a light source for emitting light to the measurement specimen, receives fluorescence and scattered light that occur when the light emitted from the light source illuminates the measurement specimen, and obtains fluorescence intensity information that corresponds to intensity of the received fluorescence and scattered light intensity information that corresponds to intensity of the received scattered light; and
    a controller configured for performing operations comprising:
        (a) classifying aggregate reticulocytes contained in the blood from other blood cells, based on the fluorescence intensity information and the scattered light intensity information obtained by the characteristic information obtaining section; and
        (b) outputting information regarding a number of the classified aggregate reticulocytes, wherein
    the operation (a) comprises:
        demarcating a red-blood-cell type coordinate area containing red blood cells and reticulocytes, in a two-dimensional coordinate having a coordinate axis representing the fluorescence intensity and a coordinate axis representing the scattered light intensity;
        obtaining a frequency distribution, with respect to the fluorescence intensity of blood cells within the red-blood-cell type coordinate area;
        obtaining fluorescence intensity X that corresponds to a peak of the frequency distribution and a variance σ of the frequency distribution from the frequency distribution;
        performing calculation of Thr=X+σ·α based on the obtained fluorescence intensity X, the obtained variance σ, and a coefficient α that is applied to measurement of the aggregate reticulocytes of the animal, thereby calculating a threshold value Thr of the fluorescence intensity; and
        demarcating an aggregate-type coordinate area that includes the aggregate reticulocytes, in the red-blood-cell type coordinate area by using the Thr of the fluorescence intensity.

2. The animal blood cell measuring apparatus of claim 1, wherein the operations further comprise
    (c) obtaining a number of the aggregate reticulocytes, based on a number of plot data contained in the aggregate-type coordinate area, and
    wherein the outputted information regarding the number of the aggregate reticulocytes is the obtained number of the aggregate reticulocytes.

3. The animal blood cell measuring apparatus of claim 1, wherein the animal is a feline.

4. The animal blood cell measuring apparatus of claim 1:
    wherein the operations further comprise receiving a selection of an animal species to be measured from at least a first animal species and a second animal species;
    wherein
    when a selection of the first animal species is received, the controller classifies the aggregate reticulocytes contained in the blood from the other blood cells, and when a selection of the second animal species is received, the controller classifies reticulocytes contained in the blood from other blood cells.

5. The animal blood cell measuring apparatus of claim 4, wherein
    the first animal species is a feline, and the second animal species is a canine.

6. The animal blood cell measuring apparatus of claim 1, wherein
    the coefficient α is set to be greater, by a predetermined magnitude, than the coefficient α that is applied when a coordinate area of reticulocytes is demarcated in the two-dimensional coordinate that represents blood of an animal species whose reticulocytes do not contain aggregate reticulocytes.

7. The animal blood cell measuring apparatus of claim 6, wherein
    the coefficient α is set to be double the coefficient α that is applied when the coordinate area of reticulocytes is demarcated in the two-dimensional coordinate that represents the blood of the animal species whose reticulocytes do not contain aggregate reticulocytes.

8. An animal blood cell measuring apparatus, comprising:
    a specimen preparation section for preparing a measurement specimen from blood of an animal and a stain solution;
    a characteristic information obtaining section which comprises a light source for emitting light to the measurement specimen, receives fluorescence and scattered light that occur when the light emitted from the light source illuminates the measurement specimen, and obtains fluorescence intensity information that corresponds to intensity of the received fluorescence and scattered light intensity information that corresponds to intensity of the received scattered light; and a controller configured for performing operations, comprising:
  (a) receiving a selection of an animal species to be measured from at least a first animal species and a second animal species;
  (b) classifying aggregate reticulocytes contained in the blood from other blood cells, based on the fluorescence intensity information and the scattered light intensity information obtained by the characteristic information obtaining section when a selection of the first animal species is received; and
  (c) outputting information regarding a number of the classified reticulocytes, wherein the operation (b) comprises:
  demarcating a red-blood-cell type coordinate area containing red blood cells and reticulocytes, in a two-dimensional coordinate having a coordinate axis representing the fluorescence intensity and a coordinate axis representing the scattered light intensity;
  obtaining a frequency distribution, with respect to the fluorescence intensity, of blood cells within the red-blood-cell type coordinate area;
  obtaining fluorescence intensity X that corresponds to a peak of the frequency distribution and a variance $\sigma$ of the frequency distribution from the frequency distribution;
  performing calculation of $Thr=X+\sigma\cdot\alpha$ a based on the obtained fluorescence intensity X, the obtained variance $\sigma$, and a coefficient $\alpha$ that is applied to measurement of the aggregate reticulocytes of the animal, thereby calculating a threshold value Thr of the fluorescence intensity; and
  demarcating an aggregate-type coordinate area that includes the aggregate reticulocytes, in the red-blood-cell type coordinate area by using the Thr of the fluorescence intensity.

9. The animal blood cell measuring apparatus of claim 8, wherein the first animal species is a feline, and the second animal species is a canine.

10. The animal blood cell measuring apparatus of claim 8, wherein
  the operation (b) comprises classifying reticulocytes contained in the blood from other blood cells based on the fluorescence intensity information and the scattered light intensity information obtained by the characteristic information obtaining section when a selection of the second animal species is received.

* * * * *